US008709731B2

(12) United States Patent
Nakamura et al.

(10) Patent No.: US 8,709,731 B2
(45) Date of Patent: Apr. 29, 2014

(54) DKK1 ONCOGENE AS THERAPEUTIC TARGET FOR CANCER AND A DIAGNOSING MARKER

(75) Inventors: Yusuke Nakamura, Tokyo (JP); Yataro Daigo, Tokyo (JP); Shuichi Nakatsuru, Kanagawa (JP)

(73) Assignee: Oncotherapy Science, Inc. (JP)

( * ) Notice: Subject to any disclaimer, the term of this patent is extended or adjusted under 35 U.S.C. 154(b) by 367 days.

(21) Appl. No.: 12/674,660

(22) PCT Filed: Aug. 21, 2008

(86) PCT No.: PCT/JP2008/002270
§ 371 (c)(1),
(2), (4) Date: May 27, 2010

(87) PCT Pub. No.: WO2009/028158
PCT Pub. Date: Mar. 5, 2009

(65) Prior Publication Data
US 2011/0076280 A1    Mar. 31, 2011

Related U.S. Application Data

(60) Provisional application No. 60/957,873, filed on Aug. 24, 2007.

(51) Int. Cl.
*G01N 33/53*    (2006.01)
(52) U.S. Cl.
USPC .......................................................... 435/7.1
(58) Field of Classification Search
None
See application file for complete search history.

(56) References Cited

U.S. PATENT DOCUMENTS

| 2009/0123368 A1 | 5/2009 | Qin et al. |
| 2009/0208514 A1 | 8/2009 | Nakamura et al. |

FOREIGN PATENT DOCUMENTS

| CN | 1963511 A | 5/2007 |
| JP | 2006-217844 A | 8/2006 |
| JP | 2007/508020 A | 4/2007 |
| WO | 2005/033343 A2 | 4/2005 |
| WO | WO 2005/033343 A2 | 4/2005 |
| WO | WO 2007/013671 A2 | 2/2007 |
| WO | WO 2007/104181 A1 | 9/2007 |

OTHER PUBLICATIONS

Baker and Kaprio. Common susceptibility genes for cancer: search for the end of the rainbow. British Medical Journal, 2006. vol. 332, pp. 1150-1152.*
Janssens, Verlinden, Gungor, Raus, and Michiels. Protein biomarkers for breast cancer prevention. European Journal of Cancer Prevention, 2004. vol. 13, pp. 307-317.*
Yamabuki et al (Cancer Research, 2007, 67(6): 2517-2525).*
Politou et al (Int J Cancer, 2006, 119: 1728-1731).*
Leitzel et al (Proceedings of the AACR Annual Meeting, 2007, vol. 48, Abstract 2665).*
Brett (Fam Pract, 1998, 15(6): 529-533).*
U.S. Appl. No. 13/246,639, filed Sep. 27, 2011, 164 pages.
Yaccoby, S. et al., "Antibody-based inhibition of DKK1 suppresses tumor-induced bone resorption and multiple myeloma growth in vivo," *Blood*, vol. 109(5), pp. 2106-2111 (Mar. 1, 2007, Epub Oct. 26, 2006).
Niehrs, C., "Function and biological roles of the Dickkopf family of Wnt modulators," *Oncogene*, vol. 25(57), pp. 7469-7481 (Dec. 4, 2006).
Wirths, O., et al., "Overexpression of Human Dickkopf-1, an Antagonist of wingless/WNT Signaling, in Human Hepatoblastomas and Wilms' Tumors," *Lab Invest.*, vol. 83(3), pp. 429-434 (Mar. 2003).
Yamabuki, T., et al., "Dikkopf-1 as a Novel Serologic and Prognostic Biomarker for Lung and Esophageal Carcinomas," *Cancer Res.*, vol. 67(6), pp. 2517-2525 (Mar. 15, 2007).
Molecular Biology of the Cell, Garland Science, 5th Edition, p. 414 (2007).

* cited by examiner

*Primary Examiner* — Sean Aeder
(74) *Attorney, Agent, or Firm* — Kilpatrick Townsend & Stockton LLP

(57)    ABSTRACT

Described herein are antibodies and antibody fragments capable of treating or preventing cancers associated with the over-expression and/or up-regulation of DKK1. Also disclosed are methods of treating or preventing cancer using the antibody and methods and kits utilized to diagnosing cancer. The herein described products and methods find utility in the context of a variety of cancers, such as pancreatic cancer, gastric cancer, liver cancer, prostate cancer, breast cancer, cervical cancer, bile duct cancer, lung cancer and esophageal cancer.

6 Claims, 5 Drawing Sheets

Fig. 2
A
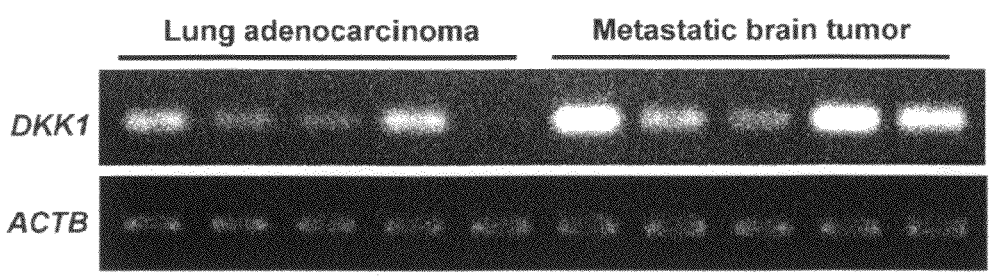
B
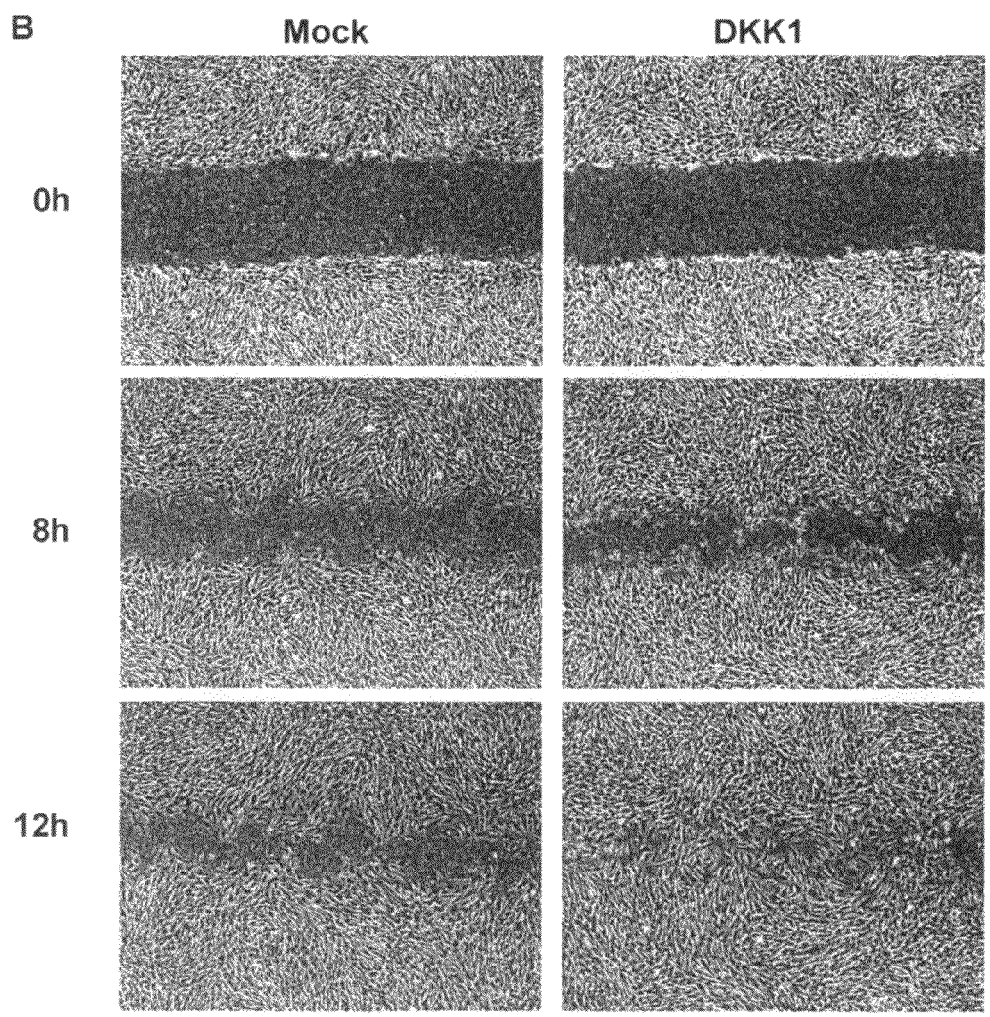

Fig. 3
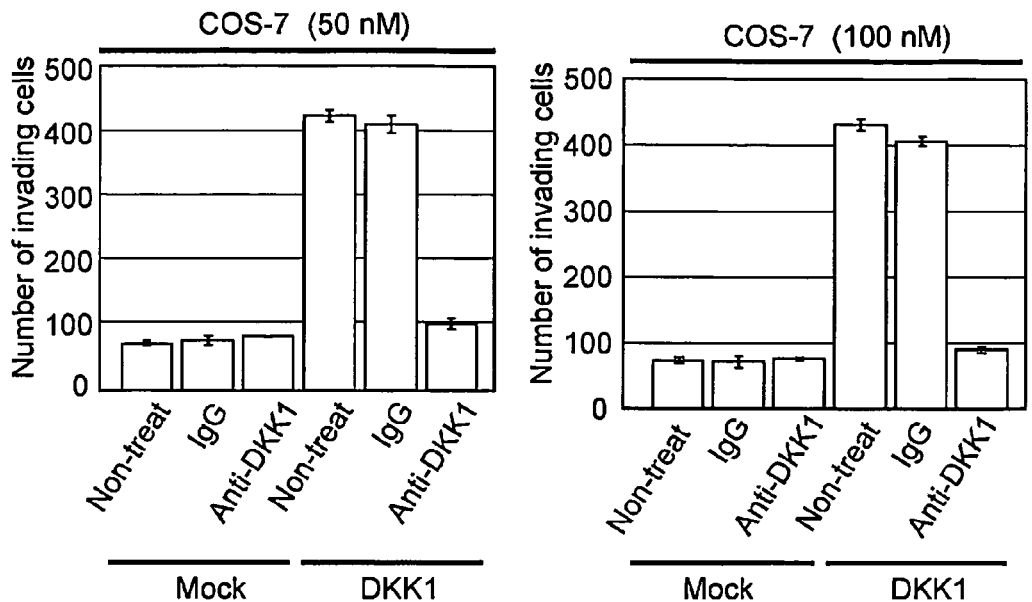
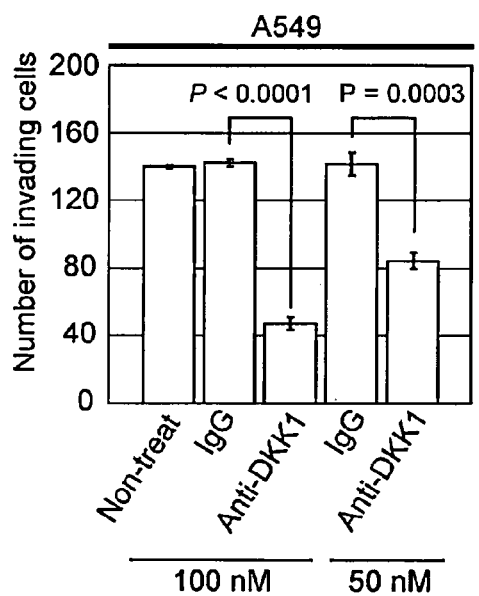
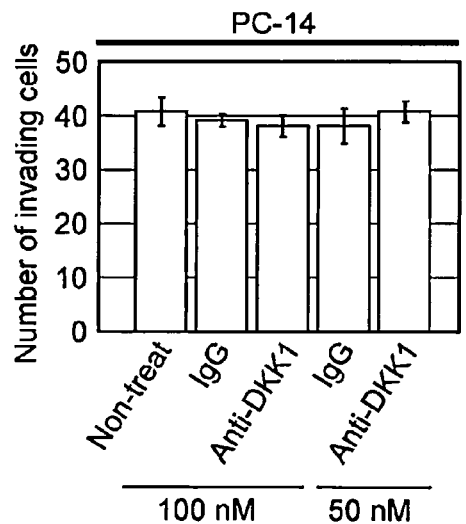

Fig. 4
A
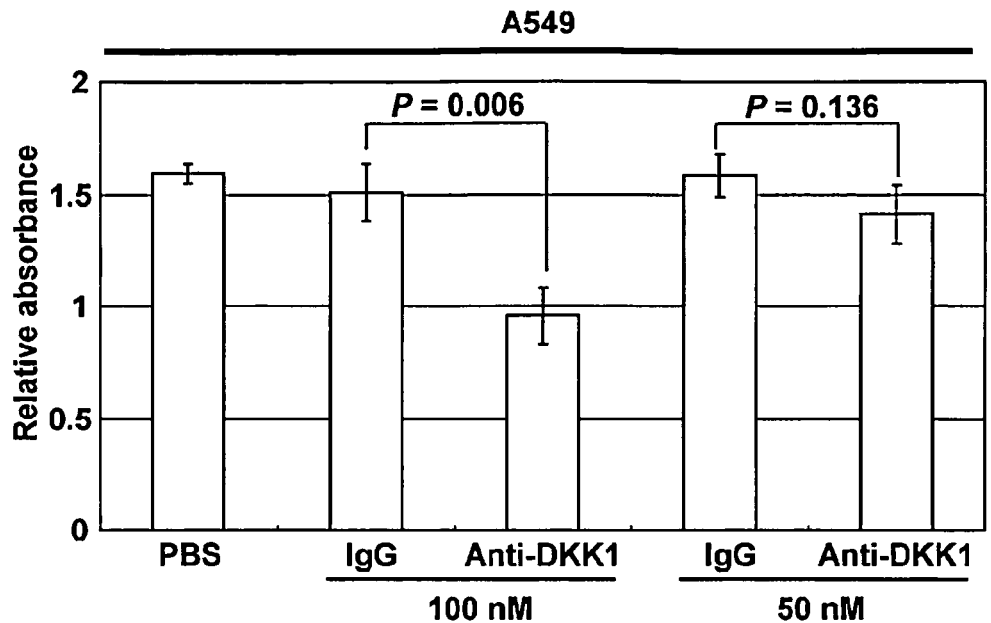
B
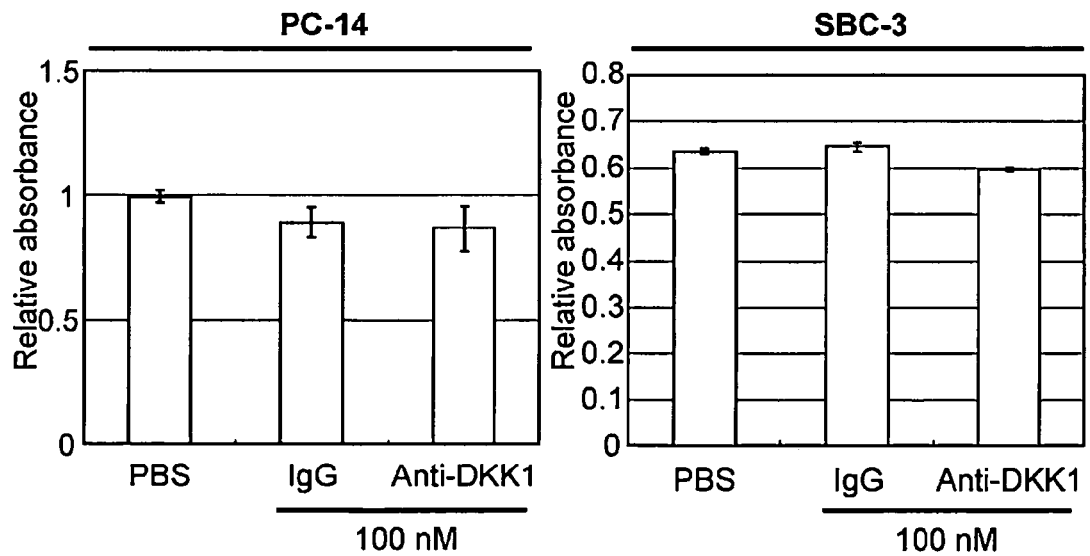

Fig. 5
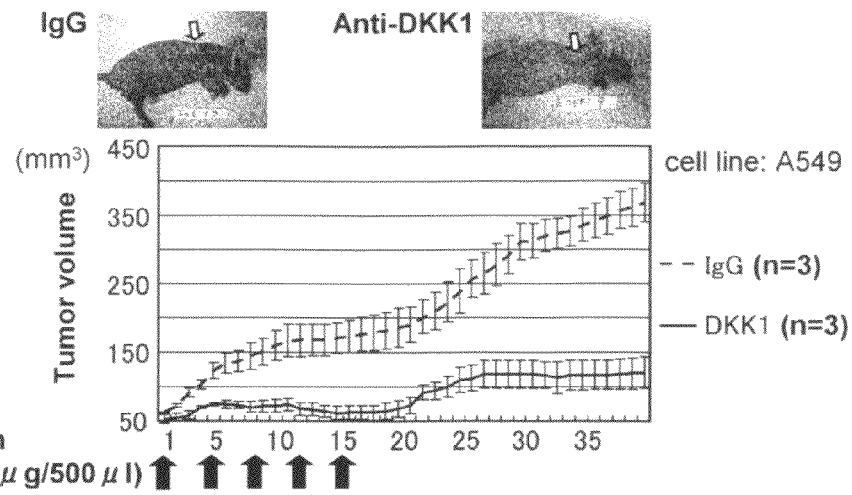
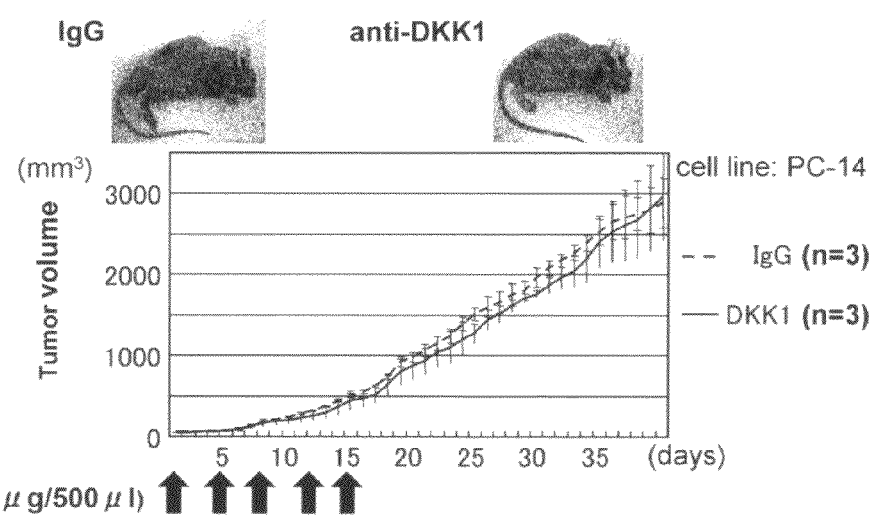
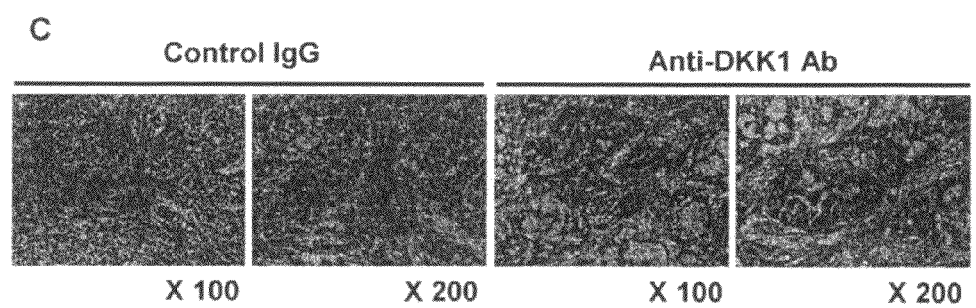

DKK1 ONCOGENE AS THERAPEUTIC TARGET FOR CANCER AND A DIAGNOSING MARKER

This application is a U.S. National Stage Application of PCT/JP2008/002270, filed Aug. 21, 2008, which claims the benefit of U.S. Provisional Application Ser. No. 60/957,873 filed Aug. 24, 2007, the contents of which are hereby incorporated by reference in their entirety.

TECHNICAL FIELD

The present invention relates to the field of biological science, more specifically to the field of cancer therapy and diagnosis. In particular, the present invention relates to a method for diagnosing and prognosing cancer and compositions and methods for inhibiting cancer cell proliferation.

BACKGROUND OF THE INVENTION

DKK1 (SEQ ID NO:1) encodes a secreted protein which plays a crucial role in head formation in vertebrate development, and is known as a negative regulator of the Wnt-signaling pathway in colon cancer cells (Niida A. et al. Oncogene 2004; 23:8520-6, Gonzalez-Sancho J M. et al. Oncogene 2005; 24:1098-103). The over-expression of DKK1 was previously reported as periodically arising in hepatoblastomas, Wilms' tumors, hepatocellular carcinomas (HCC), prostate cancer, and breast cancer, indicating a potential oncogenic function of DKK1 (Wirths O. et al. Lab Invest 2003; 83:429-34, Patil M A. et al. Oncogene 2005; 24:3737-47, Hall C L. et al. Cancer Res. 2005; 65:7554-60, Forget M A. et al. Br J Cancer. 2007; 96:646-53). In addition, serum concentrations of DKK1 protein have been shown to be increased in patients with multiple myeloma (Politou M C. et al. Int J Cancer. 2006; 119:1728-31). Furthermore, inhibition of DKK1 using an anti-DKK1 antibody has been shown to reverse the bone-destructive rheumatoid arthritis in mice to the bone-forming osteoarthritis (Diarra D et al. Nat. Med. 2007; 13:156-63). More recently, Yaccoby et al. demonstrated that antibody-based inhibition of DKK1 could suppress tumor-induced bone resorption and multiple myeloma growth in vivo. Specifically, daily subcutaneous injection of a neutralizing DKK1 antibody in the area surrounding myelomatous bone was shown to ameliorate bone turnover, presumably by increasing osteoblastogenesis and reducing osteoclastgenesis (Blood. 2007; 109:2106-11).

The role of DKK1 in promoting the development of bone lesions has also been studied in prostate cancer. PC-3, the osteolytic cancer cell line, was shown to revert to an osteoblastic phenotype when transfected with shRNA targeting DKK1. In addition, transfection of DKK1 into the osteoblastic prostate cancer cell line C4-2B, which normally induces a mix of osteoblastic and osteolytic lesions, caused the cells to develop osteolytic tumors in SCID mice (Hall C L. et al. Cancer Res. 2005; 65:7554-60).

The present inventors have screened for therapeutic target molecules using the following strategy: (I) Identifying up-regulated genes in lung cancer by genome-wide cDNA microarray system (Kikuchi T et al. Oncogene. 2003; 22:2192-205, Kikuchi T et al. Int J Oncol 2006; 28:799-805, Kakiuchi S et al. Mol Cancer Res 2003; 1:485-99, Kakiuchi S et al. Hum Mol. Genet. 2004; 13:3029-43, Taniwaki M et al. Int J Oncol 2006; 29:567-75, Yamabuki T et al. Int J Oncol: 2006; 28: 1375-84), (II) Verifying the candidate genes for its no or very low level of expression in normal tissues by northern-blotting (Saito-Hisaminato A et al. DNA Res. 2002; 9:35-45, Ochi K et al. J Hum Genet. 2003; 48:177-82), (III) Validating the biological significance of over-expression using tissue microarrays containing hundreds of archived lung-cancer samples and RNAi assay (Kato T et al. Cancer Res. 2005; 65:5638-46, Furukawa C. et al. Cancer Res. 2005; 65:7102-10, Ishikawa N et al. Cancer Res. 2005; 65:9176-84, Suzuki C et al. Cancer Res. 2005: 65:11314-11325, Ishikawa N et al. Cancer Sci. 2006; 97:737-745, Takahashi K et al. Cancer Res. 2006; 66:9408-9419), (IV) Evaluating usefulness as a serum diagnostic/prognostic biomarker for lung cancer by ELISA (Ishikawa N et al. Cancer Res. 2005; 65:9176-84, Ishikawa N et al. Clin Cancer Res. 2004; 10:8363-70. Yamabuki T et al. Cancer Res 2007; 67:2517-2525), if they are tumor-specific trans-membrane or secretory proteins.

Using this approach, the inventors recently identified Dickkopf-I (DKK1) as a novel serological and histochemical biomarker as well as a therapeutic target for lung and esophageal cancers (WO2007/01367 1, Yamabuki T. et al. Cancer Res 2007; 67:2517-2525, the contents of which are incorporated by reference). A high level of DKK1 expression was associated with poor prognosis of patients with non-small cell lung cancer (NSCLC) as well as esophageal squamous cell carcinoma (ESCC). In addition, present inventors identified that exogenous expression of DKK1 increased the invasive activity of mammalian cells, suggesting that DKK1 may play a significant role in progression of human cancer. An ELISA system was established to measure serum levels of DKK1 and found that serum DKK1 levels were significantly higher in lung and esophageal cancer patients than in healthy controls. From these findings, the inventors then focused on DKK1 as a potential target for the generation of therapeutic antibodies applicable to cancer patients.

BRIEF SUMMARY OF THE INVENTION

Taken together, current evidence suggests that an anti-DKK1 antibody may be an ideal therapeutic reagent to inhibit cancer cell proliferation, metastasis, and bone absorption in certain types of human cancers including at least cancers originated from prostate, melanocyte, and lung. Moreover, serum DKK1 may prove to be a safe and less invasive biomarker for identifying patients who should receive anti-DKK1 therapy. These studies notwithstanding, there has been little documented confirmation of DKK1 as a diagnostic and therapeutic target.

Thus, in view of the foregoing, it is an object of the present invention to provide novel methods for diagnosing, prognosing and treating various types of cancer. To that end, the present invention examines the value of DKK1, as a biomarker detecting various human cancers and investigates the possibility of using a DKK1 antibody to inhibit cancer cell invasion and growth. More particularly, the present invention discloses the elevated expression of the DKK1 transcript in cancer samples in five organs (pancreas, stomach, liver, prostate, and mammary glands). The present invention also discloses the presence of high levels of DKK1 protein in serologic samples from patients with cancers of the pancreas, stomach, liver, prostate, breast, bile duct, and uterus. Furthermore, an anti-DKK1 antibody that inhibits invasion of cancer cells as well as DKK1-over-expressed mammalian cells in vitro is disclosed. Moreover, the anti-DKK1 antibody significantly suppressed cancer growth in vitro and in BALB/C mice inoculated with A549 cells. These data confirm the utility of DKK1 as a serum biomarker for screening wide range of cancers, as well as the utility of anti-DKK1 antibody as a candidate therapeutic agent for the treatment of cancer metastasis and proliferation.

Accordingly, it is an object of the present invention to provide an antibody or antibody fragment capable of binding to a DKK1 protein or a partial peptide thereof that possesses suppression activity in the context of a DKK1 associated cancer.

It is another object of the present invention to provide methods for treating cancer, inhibiting the metastasis, invasion or migration of cancer by administering an effective amount of at least one anti-DKK1 antibody or antibody fragment with a pharmaceutical acceptable carrier.

It is a further object of the present invention to provide a pharmaceutical composition that contains at least one anti-DKK1 antibody or antibody fragment thereof useful in the treatment of cancer or inhibition for the metastasis, invasion or migration of cancer.

It is yet a further object of the present invention to provide a method of screening for an anti-DKK1 antibody having potential therapeutic activity by screening a population of anti-DKK1 antibodies for those that inhibit proliferation of cancer cells.

It is yet a further object of the present invention to provide a method for diagnosing cancer or a predisposition for developing cancer, a cancer metastasis, a cancer invasion or a cancer cell migration in a subject, by determining the expression level of DKK1 gene in a subject-derived biological sample, wherein an increase in the expression level as compared to a normal control level of the gene indicates that the subject suffers from or is at a risk of developing cancer, a cancer metastasis, a cancer invasion or a cancer cell migration.

It is yet a further object of the present invention to provide a kit for diagnosing cancer or a predisposition for developing cancer, a cancer metastasis, a cancer invasion or a cancer cell migration in a subject.

It is yet a further object of the present invention to provide immunoassay reagents for detecting DKK1 that include an anti-DKK1 antibody. An anti-DKK1 antibody may be a polyclonal antibody, monoclonal antibody, or at least two monoclonal antibodies that each recognize different antigenic determinants of DKK1.

It is yet a further object of the present invention to provide a method of screening for a compound for treating a cancer, wherein the method includes the step of contacting a DKK1 polypeptide with a test compound; and selecting the test compound that suppresses the biological activity of the DKK1 polypeptide.

In one embodiment, the present invention provides for the use of an anti-DKK1 antibody or antibody fragment of the present invention in manufacturing a pharmaceutical composition for treating, inhibiting the metastasis, invasion or migration of a cancer characterized by either or both of the over-expression and up-regulation of DKK1.

In another embodiment, the present invention provides an anti-DKK1 antibody or antibody fragment for treating, inhibiting the metastasis, invasion or migration of a cancer characterized by either or both of the over-expression and up-regulation of DKK1.

In yet a further embodiment, the present invention provides a method or process for manufacturing a pharmaceutical composition for treating, inhibiting the metastasis, invasion or migration of a cancer characterized by either or both of the over-expression and up-regulation of DKK1, wherein the method or process includes the step of formulating a pharmaceutically or physiologically acceptable carrier with anti-DKK1 antibody or antibody fragment as active ingredients.

In yet another embodiment, the present invention provides a method or process for manufacturing a pharmaceutical composition for treating, inhibiting the metastasis, invasion or migration of a cancer characterized by either or both of the over-expression and up-regulation of DKK1, wherein the method or process includes the step of admixing an active ingredient with a pharmaceutically or physiologically acceptable carrier, wherein the active ingredient is anti-DKK1 antibody or antibody fragment.

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment, and not restrictive of the invention or other alternate embodiments of the invention.

BRIEF DESCRIPTION OF THE DRAWINGS

Various aspects and applications of the present invention will become apparent to the skilled artisan upon consideration of the brief description of the figures and the detailed description of the present invention and its preferred embodiments that follows:

FIG. 2 depicts the effects of DKK1 expression. Panel (A) depicts the expression of DKK1 in clinical samples of earlier primary ADC (stage I-III A), advanced primary ADC (stage III B-IV), and metastatic brain tumor from ADC, examined by semi-quantitative RT-PCR. Panel (B) depicts the results of wound migration assays, using COS-7 cells transfected with DKK1-expressing plasmids or mock vectors.

FIG. 3 depicts the inhibition of cell invasive activity by an anti-DKK1 antibody. Panel (A) depicts the results of matrigel invasion assays evaluating the effect of an anti-DKK1 antibody (50 or 100 nM; y-axis) on the invasion of COS-7 cells transiently transfected with DKK1 expressing plasmids. Cellular invasion caused by DKK1 over-expression and/or up-regulation was suppressed by addition of anti-DKK1 antibody into their culture media. Each experiment was done in triplicate. Panel (B) and (C) depict the results of matrigel invasion assays evaluating the effect of an anti-DKK1 antibody (50 or 100 nM; y-axis) on the invasion of a DKK1-over-expressing NSCLC cell line A549 (B) and a non-DKK1-expressing NSCLC cell line, PC-14 (C). The cellular invasion of A549 cells detected using matrigel assays was suppressed by addition of an anti-DKK1 antibody into the culture media, in a dose-dependent manner, while that of PC-14 cells expressing DKK1 at a barely-detectable level was not affected. Each experiment was done in triplicate.

FIG. 4 depicts the inhibition of cell growth by an anti-DKK1 antibody in vitro. Panel (A) depicts the results of an MTT assay evaluating the effect of an anti-DKK1 antibody (50 or 100 nM; y-axis) on the growth of a DKK1-over-expressing NSCLC cell line A549, and panel (B) depicts the results of an MTT assay evaluating the effect of an anti-DKK1 antibody (100 nM; y-axis) on the growth of a non-DKK1-expressing NSCLC cell line, PC-14 and SBC-3. The cell growth of A549 cells detected using MTT assays was suppressed by addition of an anti-DKK1 antibody into the culture media, in a dose-dependent manner, while that of PC-14 and SBC-3 cells expressing DKK1 at a barely-detectable level was not affected. Each experiment was done in triplicate.

FIG. 5 depicts the growth suppressive effect of an anti-DKK1 antibody to DKK1-expressing lung cancer cells that were transplanted to nude mice and histopathological examination with anti-DKK1 antibody. Panel (A) and (B) depict the average tumor volumes of 3 mice treated with anti-DKK1 antibody or IgG (control) were plotted. Animals were administered with each of the antibodies (100 micro-g/500 micro-/animal at days 1, 3, 5, 7, and 9 [a total of 5 injections]) by intraperitoneal injection. Growth of grafted tumors derived from DKK1-expressing A549 cells was significantly suppressed by anti-DKK1 antibody (A), while that of PC-14 cells that hardly express DKK1 was not affected (B). Panel (C) depicts the results of histopathological examination of HE-stained tumors (A549) treated with anti-DKK1 antibody. Significant fibrosis and decrease in viable cancer cell numbers in anti-DKK1 antibody-treated tumor tissues compared with those treated with control IgG was observed.

DETAILED DESCRIPTION OF THE INVENTION

Figure 1:
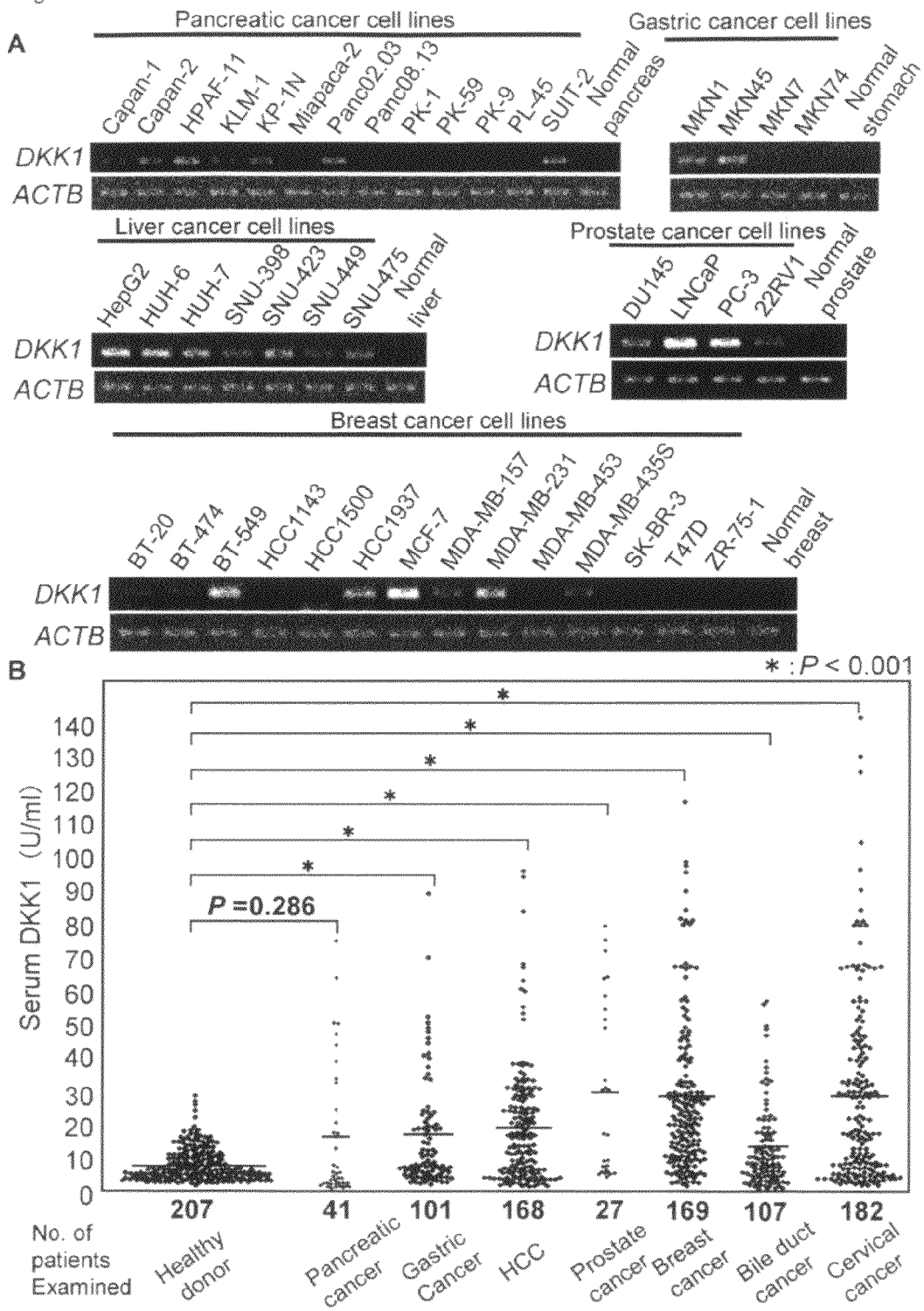
FIG. 1 depicts DKK1 expression in various cancer cells and serum levels of DKK1 in cancer patients. Panel (A) depicts the elevated expression of a DKK1 transcript in clinical cancer tissues in several organs (pancreas, stomach, liver, prostate and mammary glands). Panel (B) depicts serum levels of DKK1 in various kinds of cancer patients. The levels of serum DKK1 protein were significantly higher in cancer patients than in healthy donors ($P<0.001$; Mann-Whitney U test), except pancreatic cancers ($P=0.286$; Mann-Whitney U test). Black lines, average serum level.

Although methods and materials similar or equivalent to those described herein can be used in the practice or testing of embodiments of the present invention, the preferred methods and materials are now described. However, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the present invention which will be limited only by the appended claims.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the present invention, the following definitions apply:

DEFINITIONS

The words "a", "an", and "the" as used herein mean "at least one" unless otherwise specifically indicated As used herein, the term "organism" refers to any living entity composed of at least one cell. A living organism can be as simple as, for example, a single eukaryotic cell or as complex as a mammal, including a human being.

As used herein, the term "biological sample" refers to a whole organism or a subset of its tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen). The term "biological sample" further refers to a homogenate, lysate, extract, cell culture or tissue culture prepared from a whole organism or a subset of its cells, tissues or component parts, or a fraction or portion thereof. Lastly, "biological sample" refers to a medium, such as a nutrient broth or gel in which an organism has been propagated, which contains cellular components, such as proteins or polynucleotides.

The terms "polypeptide", "peptide", and "protein" are used interchangeably herein to refer to a polymer of amino acid residues. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers. The terms "polynucleotides", "oligonucleotides" "nucleotides", "nucleic acids", and "nucleic acid molecules" are used interchangeably herein to refer to a polymer of nucleic acid residues and, unless otherwise specifically indicated, are similarly to the amino acids referred to by their commonly accepted single-letter codes. Similar to the amino acids, they encompass both naturally-occurring and non-naturally occurring nucleic acid polymers.

Antibody

The term "antibody" as used herein is intended to include immunoglobulins and fragments thereof which are specifically reactive to the designated protein or peptide thereof. The present invention provides an antibody that specifically binds to the polypeptide of DKK1. In a preferred embodiment, the present invention provides an antibody that binds to the DKK1 amino acid sequence of SEQ ID NO: 2. Antibodies of the present invention can include human antibodies, primatized antibodies, chimeric antibodies, bispecific antibodies, humanized antibodies, antibodies fused to other proteins, chemicals or radiolabels, and antibody fragments. Furthermore, an antibody herein is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity. An "antibody" indicates all classes (e.g. IgA, IgD, IgE, IgG and IgM). "Antibody fragments" include a portion of an intact antibody, generally the antigen binding or variable region of the intact antibody. Examples of antibody fragments include Fab, Fab', F(ab')2, and Fv fragments; linear antibodies; and single chain antibody molecules.

Production of Antibodies

The subject invention uses antibodies to DKK1. These antibodies may be provided by known methods.

Exemplary techniques for the production of the antibodies used in accordance with the present invention are herein described.

(i) Polyclonal Antibodies:

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOC12, or R'N=C=NR, where R' and R are different alkyl groups.

Animals are immunized against the antigen, immunogenic conjugates, or derivatives by combining, e.g. 100 micro-g or 5 micro-g of the protein or conjugate (for rabbits or mice, respectively) with 3 volumes of Freund's complete adjuvant and injecting the solution intradermally at multiple sites. One month later the animals are boosted with ⅕ to 1/10 the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent.

Conjugates also can be made in recombinant cell culture as protein fusions. Also, aggregating agents such as alum are suitably used to enhance the immune response.

(ii) Monoclonal Antibodies:

Monoclonal antibodies may be obtained from a population of substantially homogeneous antibodies, i.e., the individual antibodies contained within the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., Nature, 256: 495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Manassas, Va., USA. Human myeloma and mouse-human heteromyeloma cell lines also have been described for the production of human monoclonal antibodies (Kozbor, J. Immunol., 133: 300 1 (1984); Brodeur et al., Monoclonal Antibody Production Techniques and Applications, pp. 51-63 (Marcel Dekker, Inc., New York, 1987)).

Culture media in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., Anal. Biochem., 107: 220 (1980).

After hybridoma cells that produce antibodies of the desired specificity, affinity, and/or activity are identified, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones may be suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies may be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., Curr. Opinion in Immunol., 5: 256-262 (1993) and Pluckthun, Immunol. Revs., 130: 151-188 (1992).

Another method of generating specific antibodies, or antibody fragments, reactive against a DKK1 involves the screening of expression libraries encoding immunoglobulin genes, or portions thereof, expressed in bacteria with a DKK1 protein or peptide. For example, complete Fab fragments, VH regions and Fv regions can be expressed in bacteria using phage expression libraries. See for example, Ward et al., Nature 341: 544-546 (1989); Huse et al., Science 246: 1275-1281 (1989); and McCafferty et al., Nature 348: 552-554 (1990). Screening such libraries with, for example, a DKK1 peptide, can identify immunoglobulin fragments reactive with DKK1. Alternatively, the SCID-hu mouse (available from Genpharm) can be used to produce antibodies or fragments thereof.

In a further embodiment, antibodies or antibody fragments can be isolated from antibody phage libraries generated using the techniques described in McCafferty et al., Nature, 348: 552-554 (1990). Clackson et al., Nature, 352: 624-628 (1991) and Marks et al., J Mol Biol, 222: 581-597 (1991) describe the isolation of murine and human antibodies, respectively, using phage libraries. Subsequent publications describe the production of high affinity (nM range) human antibodies by chain shuffling (Marks et al., BioTechnology, 10: 779-783 (1992)), as well as combinatorial infection and in vivo recombination as a strategy for constructing very large phage libraries (Waterhouse et al., Nuc. Acids. Res., 21: 2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., Proc. Natl. Acad. Sci. USA, 81: 6851 (1984)), or by covalently joining to the immunoglobulin coding sequence all or part of the coding sequence for a non-immunoglobulin polypeptide.

Typically, such non-immunoglobulin polypeptides are substituted for the constant domains of an antibody, or they are substituted for the variable domains of one antigen combining site of an antibody to create a chimeric bivalent antibody having one antigen-combining site with specificity for a first antigen and another antigen-combining site with specificity for a different antigen.

(iii) Humanized Antibodies:

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321: 522-525 (1986); Reichmann et al., Nature, 332: 323-327 (1988); Verhoeyen et al., Science, 239: 1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hyper-variable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Suns et al., J. Immunol., 151: 2296 (1993); Chothia et al., J. Mol. Biol, 196: 901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89: 4285 (1992); Presta et al., J. Immunol., 151: 2623 (1993)).

It is preferable that antibodies to be humanized retain high affinity for the antigen and other favorable biological properties. To achieve this goal, according to a preferred method, humanized antibodies may be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen, is achieved. In general, the hypervariable region residues are directly and most substantially involved in influencing antigen binding.

(iv) Human Antibodies:

As an alternative to humanization, human antibodies can be generated. For example, it is possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ line mutant mice will result in the production of human antibodies upon antigen challenge. See, e.g., Jakobovits et al., Proc. Mad. Acad. Sci. USA, 90: 255 1 (1993); Jakobovits et al., Nature, 362: 255-258 (1993); Bruggermann et al., Year in Immuno., 7: 33 (1993); and U.S. Pat. Nos. 5,591,669, 5,589, 369 and 5,545,807.

Alternatively, phage display technology (McCafferty et al., Nature 348: 552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S. and Chiswell, David J., Current Opinion in Structural Biology 3: 564-57 1 (1993). Several sources of V-gene segments can be used for phage display.

Clackson et al., Nature, 352: 624-628 (1991) isolated a diverse array of antioxazolone antibodies from a small random combinatorial library of V genes derived from the spleens of immunized mice. A repertoire of V genes from unimmunized human donors can be constructed and antibodies to a diverse array of antigens (including self antigens) can be isolated essentially following the techniques described by Marks et al., J. Mol. Biol, 222: 581-597 (1991), or Griffith et al., EMBO J. 12: 725-734 (1993). See, also, U.S. Pat. Nos. 5,565,332 and 5,573,905.

Human antibodies may also be generated by in vitro activated B cells (see U.S. Pat. Nos. 5,567,610 and 5,229,275). A preferred means of generating human antibodies using SCID mice is disclosed in commonly-owned, co-pending applications.

(v) Antibody Fragments:

Various techniques have been developed for the production of functional antibody fragments. In the context of the present invention, the antibody fragment may include a variable region or antigen-binding region of the antibody. Traditionally, these fragments were derived via proteolytic digestion of intact antibodies (see, e.g., Morimoto et al., Journal of Biochemical and Biophysical Methods 24: 107-117 (1992) and Brennan et al., Science, 229: 81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F (ab') 2 fragments (Carter et al., Bio/Technology 10: 163-167 (1992)). According to another approach, F (ab') 2 fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a "linear antibody", e.g., as described in U.S. Pat. No. 5,641,870 for example. Such linear antibody fragments may be monospecific or bispecific.

(vi) Bispecific Antibodies:

Bispecific antibodies are antibodies that have binding specificities for at least two different epitopes. Exemplary, an anti-cancer cell marker (e.g. DKK1) binding arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIH (CD 16) so as to focus cellular defense mechanisms to the cancer cell. Bispecific antibodies may also be used to localize cytotoxic agents to the cancer cell. These antibodies possess a cancer cell marker-binding arm and an arm that binds the cytotoxic agent (e.g. saporin, anti-interferon-a, vinca alkaloid, ricin A chain, methotrexate or radioactive isotope hapten). Bispecific antibodies can be prepared as full length antibodies or antibody fragments (e.g. F (ab) 2 bispecific antibodies).

Methods for making bispecific antibodies are known in the art. Traditional production of full-length bispecific antibodies is based on the co-expression of two immunoglobulin heavy chain-light chain pairs, where the two chains have different specificities (Millstein et al., Nature, 305: 537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10: 3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, including at least part of the hinge, CH2, and CH3 regions. It is preferred to have the first heavy-chain constant region (CHI) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121: 210 (1986).

According to another approach described in U.S. Pat. No. 5,731,168, the interface between a pair of antibody molecules can be engineered to maximize the percentage of heterodimers which are recovered from recombinant cell culture. The preferred interface includes at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chains are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies also include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F (ab') 2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., J. Exp. Med., 175: 2 17-225 (1992) describe the production of a fully humanized bispecific antibody F (ab') 2 molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., J. Immunol. 148 (5): 1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90: 6444-6448 (1993) has provided an alternative mechanism for making bispecific antibody fragments. The fragments include a heavy-chain variable domain (VH) connected to a light-chain variable domain (VL) by a linker that is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J; Immunol., 152: 5368 (1994).

Antibodies with more than two valencies are contemplated. For example, trispecific antibodies can be prepared. Tutt et al.; J. Immunol. 147: 60 (1991).

(vii) Non-Antibody Binding Protein:

The terms "non-antibody binding protein" or "non-antibody ligand" or "antigen binding protein" interchangeably refer to antibody mimics that use non-immunoglobulin protein scaffolds, including adnectins, avimers, single chain polypeptide binding molecules, and antibody-like binding peptidomimetics, as discussed in more detail below.

Other compounds have been developed that target and bind to targets in a manner similar to antibodies. Certain of these "antibody mimics" use non-immunoglobulin protein scaffolds as alternative protein frameworks for the variable regions of antibodies.

For example, Ladner et al. (U.S. Pat. No. 5,260,203) describe single polypeptide chain binding molecules with binding specificity similar to that of the aggregated, but molecularly separate, light and heavy chain variable region of antibodies. The single-chain binding molecule contains the antigen binding sites of both the heavy and light chain variable regions of an antibody connected by a peptide linker and will fold into a structure similar to that of the two peptide antibody. The single-chain binding molecule displays several advantages over conventional antibodies, including, smaller size, greater stability and are more easily modified.

Ku et al. (Proc Natl Acad Sci USA 92(14):6552-6556 (1995)) describe an alternative to antibodies based on cytochrome b562. Ku et al. (1995) generated a library in which two of the loops of cytochrome b562 were randomized and selected for binding against bovine serum albumin. The individual mutants were found to bind selectively with BSA similarly with anti-BSA antibodies.

Lipovsek et al. (U.S. Pat. Nos. 6,818,418 and 7,115,396) describe an antibody mimic featuring a fibronectin or fibronectin-like protein scaffold and at least one variable loop. Known as Adnectins, these fibronectin-based antibody mimics exhibit many of the same characteristics of natural or engineered antibodies, including high affinity and specificity for any targeted ligand. Any technique for evolving new or improved binding proteins can be used with these antibody mimics.

The structure of these fibronectin-based antibody mimics is similar to the structure of the variable region of the IgG heavy chain. Therefore, these mimics display antigen binding properties similar in nature and affinity to those of native antibodies. Further, these fibronectin-based antibody mimics exhibit certain benefits over antibodies and antibody fragments. For example, these antibody mimics do not rely on disulfide bonds for native fold stability, and are, therefore, stable under conditions which would normally break down antibodies. In addition, since the structure of these fibronectin-based antibody mimics is similar to that of the IgG heavy chain, the process for loop randomization and shuffling can be employed in vitro that is similar to the process of affinity maturation of antibodies in vivo.

Beste et al. (Proc Natl Acad Sci USA 96(5):1898-1903 (1999)) describe an antibody mimic based on a lipocalin scaffold (Anticalin®). Lipocalins are composed of a beta-barrel with four hypervariable loops at the terminus of the protein. Beste (1999), subjected the loops to random mutagenesis and selected for binding with, for example, fluorescein. Three variants exhibited specific binding with fluorescein, with one variant showing binding similar to that of an anti-fluorescein antibody. Further analysis revealed that all of the randomized positions are variable, indicating that Anticalin® would be suitable to be used as an alternative to antibodies.

Anticalins® are small, single chain peptides, typically between 160 and 180 residues, which provides several advantages over antibodies, including decreased cost of production, increased stability in storage and decreased immunological reaction.

Hamilton et al. (U.S. Pat. No. 5,770,380) describe a synthetic antibody mimic using the rigid, non-peptide organic scaffold of calixarene, attached with multiple variable peptide loops used as binding sites. The peptide loops all project from the same side geometrically from the calixarene, with respect to each other. Because of this geometric conformation, all of the loops are available for binding, increasing the binding affinity to a ligand. However, in comparison to other antibody mimics, the calixarene-based antibody mimic does not consist exclusively of a peptide, and therefore it is less vulnerable to attack by protease enzymes. Neither does the scaffold consist purely of a peptide, DNA or RNA, meaning this antibody mimic is relatively stable in extreme environmental conditions and has a long life span. Further, since the calixarene-based antibody mimic is relatively small, it is less likely to produce an immunogenic response.

Murali et al. (Cell Mol Biol. 49(2):209-216 (2003)) describe a methodology for reducing antibodies into smaller peptidomimetics, they term "antibody like binding peptidomimetics" (ABiP) which can also be useful as an alternative to antibodies.

Silverman et al. (Nat Biotechnol. (2005), 23: 1556-1561) describe fusion proteins that are single-chain polypeptides including multiple domains termed "avimers." Developed from human extracellular receptor domains by in vitro exon shuffling and phage display the avimers are a class of binding proteins somewhat similar to antibodies in their affinities and specificities for various target molecules. The resulting multidomain proteins can include multiple independent binding domains that can exhibit improved affinity (in some cases sub-nanomolar) and specificity compared with single-epitope binding proteins. Additional details concerning methods of construction and use of avimers are disclosed, for example, in US Pat. App. Pub. Nos. 20040175756, 20050048512, 20050053973, 20050089932 and 20050221384.

In addition to non-immunoglobulin protein frameworks, antibody properties have also been mimicked in compounds including, but not limited to, RNA molecules and unnatural oligomers (e.g., protease inhibitors, benzodiazepines, purine derivatives and beta-turn mimics) all of which are suitable for use with the present invention.

As known in the art, aptamers are macromolecules composed of nucleic acid that bind tightly to a specific molecular target. Tuerk and Gold (Science. 249:505-510 (1990)) discloses SELEX (Systematic Evolution of Ligands by Exponential Enrichment) method for selection of aptamers. In the SELEX method, a large library of nucleic acid molecules (e.g., $10^{15}$ different molecules) is produced and/or screened with the target molecule. Isolated aptamers can then be further refined to eliminate any nucleotides that do not contribute to target binding and/or aptamer structure (i.e., aptamers truncated to their core binding domain). See, e.g., Jayasena, 1999, Clin. Chem. 45:1628-1650 for review of aptamer technology.

Although the construction of test agent libraries is well known in the art, herein below, additional guidance in identifying test agents and construction libraries of such agents for the present screening methods are provided.

Antibody Neutralizing DKK1 Activity

The term "neutralizing" in reference to an anti-DKK1 antibody of the invention or the phrase "antibody that neutralizes DKK1 activity" is intended to refer to an antibody whose binding to or contact with DKK1 results in inhibition of a cell proliferative activity, metastasis of cancer, invasion of cancer cells or migration of cancer cells induced by DKK1. Because the DKK1 is secreted to extracellular and functions as an essential factor of proliferation, migration, invasion and metastasis of cancer cells, some anti-DKK1 antibodies may neutralize these activity. The neutralizing antibody in this invention is especially useful in therapeutic applications: to prevent or treat intractable diseases cancers, and cancer metastasis. The neutralizing antibody in this invention can be administered to a patient, or contacted with a cell for inhibiting metastasis of a cancer characterized by either or both of the over-expression and up-regulation of DKK1.

Antibody Conjugates and Other Modifications

The antibodies used in the methods or included in the articles of manufacture herein are optionally conjugated to cytotoxic or therapeutic agent.

Therapeutic agent herein is included chemotherapeutic agent which is a chemical compound useful in the treatment of cancer. Examples of chemotherapeutic agents include, but are not limited to, the following and their pharmaceutically acceptable salts, acids and derivatives:
alkylating agents such as thiotepa and cyclophosphamide; alkyl sulfonates such as busulfan, improsulfan and piposulfan; aziridines such as benzodopa, carboquone, meturedopa, and uredopa; ethylenimines and methylmelamines including altretamine, triethylenemelamine, trietylenephosphoramide, triethylenethiophosphaoramide and trimethylolmelamine; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, ranimustine; antibiotics such as aclacinomycin, actinomycin, anthramycin, azaserine, bleomycins, cactinomycin, calicheamicin, carubicin, caminomycin, carzinophilin, chromomycin, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatrexate; defofamine; demecolcine; diaziquone; eflornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK@ razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOLO, Bristol-Myers Squibb Oncology, Princeton, N.J.) and docetaxel (TAXOTERE, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; and capecitabine; Also included in this definition are anti-hormonal agents that act to regulate or inhibit hormone action on tumors such as anti-estrogens including for example tamoxifen, raloxifene, aromatase inhibiting 4 (5)-imidazoles, 4 hydroxytamoxifen, trioxifene, keoxifene, onapristone, and toremifene (Fareston); and anti-androgens such as flutamide, nilutamide, bicalutamide, leuprolide, and goserelin; and pharmaceutically acceptable salts, acids or derivatives of any of the above.

Conjugates of an antibody and one or more small molecule toxins, such as a calicheamicin, a maytansine (U.S. Pat. No. 5,208,020), a trichothecin, and CC 1065 are also contemplated herein. In one preferred embodiment of the invention, the antibody is conjugated to one or more maytansine molecules (e.g. about 1 to about 10 maytansine molecules per antibodies molecule). Maytansine may, for example, be converted to May SS-Me which may be reduced to May-SH3 and reacted with modified antibodies (Chan et al. Cancer Research 52: 127-131 (1992)) to generate a maytansinoid-antibody conjugate.

Alternatively, an antibody may be conjugated to one or more calicheamicin molecules. The calicheamicin family of antibiotics is capable of producing double stranded DNA breaks at sub-picomolar concentrations. Structural analogues of calicheamicin which may be used include, but are not limited to gamma$_1^I$, alpha$_2^I$, alpha$_3^I$, N-acetyl-gamma$_1^I$, PSAG and theta$^I$ (Hinman et al. Cancer Research 53: 3336-3342 (1993) and Lode et al, Cancer Research 58: 2925-2928 (1998)).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha sarcin, Aleurites fordii proteins, dianthin proteins, *Phytolacca americana* proteins (PAPI, PAPII, and PAP-S), *momordica charantia* inhibitor, curcin, crotin, *saponaria officinalis* inhibitor, gelonin, mitogellin, restrictocin, phenomycin, neomycin and the trichothecenes. See, for example, WO 93/21232 published Oct. 28, 1993.

The present invention further contemplates an antibody conjugated with a variety of radioactive isotopes. Examples include $^{211}$At, $^{131}$I, $^{125}$I, $^{90}$Y, $^{186}$Re, $^{188}$Re, $^{153}$Sm, $^{212}$Bi, $^{32}$P and radioactive isotopes of Lu.

Conjugates of an antibody and a cytotoxic agent may be made using a variety of bifunctional protein coupling agents such as N-succinimidyl-3-(2-pyridylthio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al. Science 238: 1098 (1987). Carbon-14-labeled 1 isothiocyanatobenzyl-3-methyldiethylene triaminepenta acetic acid (MX-DTPA) is an exemplary chelating agent for conjugation of radionuclide to the antibody. See WO94/11026. The linker may be a "cleavable linker" facilitating release of the cytotoxic drug in the cell. For example, an acid-labile linker, peptidase-sensitive linker, dimethyl linker or disulfide-containing linker (Charm et al. Cancer Research 52: 127-131 (1992)) may be used.

Alternatively, a fusion protein containing an antibody and cytotoxic agent may be made, e.g. by recombinant techniques or peptide synthesis.

In yet another embodiment, an antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionuclide).

The antibodies of the present invention may also be conjugated with a pro-drug activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of such conjugates includes any enzyme capable of acting on a prodrug in such a way so as to convert it into its more active, cytotoxic form.

Examples of enzymes useful in the methods of the present invention include, but are not limited to, alkaline phosphatase useful for converting phosphate-containing prodrugs into free drugs; arylsulfatase useful for converting sulfate-containing prodrugs into free drugs; cytosine deaminase useful for converting nontoxic 5-fluorocytosine into the anti-cancer drug, fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydratecleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328: 457-458 (1987)). Antibody-abzyme conjugates can be prepared as described herein for delivery of the abzyme to a tumor cell population.

The enzymes of this invention can be covalently bound to an antibody by techniques well known in the art such as the use of the heterobifunctional cross linking reagents discussed above. Alternatively, fusion proteins containing at least the antigen binding region of an antibody of the invention linked to at least a functionally active portion of an enzyme of the invention can be constructed using recombinant DNA techniques well known in the art (see, e.g., Neuberger et al., Nature, 312: 604-608 (1984)).

Other antibody modifications are contemplated herein. For example, an antibody may be linked to one of a variety of nonproteinaceous polymers, e.g., polyethylene glycol, polypropylene glycol, polyoxyalkylenes, or copolymers of polyethylene glycol and polypropylene glycol.

The antibodies disclosed herein may also be formulated as liposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition that includes phosphatidylcholine, cholesterol and PEG derivatized phosphatidylethanolamine (PEG-PE). Liposomes are extruded through filters of defined pore size to yield liposomes with the desired diameter. Fab' fragments of an antibody of the present invention can be conjugated to the liposomes as described in Martin et al.; J Biol. Chem. 257: 286-288 (1982) via a disulfide interchange reaction. A chemotherapeutic agent is optionally contained within the liposome. See Gabizon et al. A National Cancer Inst. 81 (19) 1484 (1989).

Amino acid sequence modifications of antibodies described herein are contemplated. For example, it may be desirable to improve the binding affinity and/or other biological properties of the antibody. Amino acid sequence variants of the antibody are prepared by introducing appropriate nucleotide changes into the antibody encoding nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is called "alanine scanning mutagenesis" as described by Cunningham and Wells Science, 244: 1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody of an enzyme, or a polypeptide which increases the serum half-life of the antibody.

Another type of variant is an amino acid substitution variant. These variants have at least one amino acid residue in the antibody molecule replaced by different residue. The sites of greatest interest for substitutional mutagenesis of antibody include the hypervariable regions, but FR alterations are also contemplated.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Naturally occurring residues are divided into groups based on common side-chain properties:
(1) hydrophobic: norleucine, met, ala, val, leu, ile;
(2) neutral hydrophiuic: cys, ser, thr;
(3) acidic: asp, glu;
(4) basic: asn, gln, his, lys, arg;
(5) residues that influence chain orientation: gly, pro; and
(6) aromatic: tip, tyr, phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bonds may be added to the antibody to improve its stability (particularly where the antibody is a fragment such as an Fv fragment).

A particularly preferred type of substitutional variant involves substituting one or more hypervariable region residues of a parent antibody (e.g. a humanized or human antibody). Generally, the resulting variants selected for further development will have improved biological properties relative to the parent antibody from which they are generated. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hyper-variable region sites for modification, alanine scanning mutagenesis can be performed to identified hypervariable region residues contributing significantly to antigen binding. Alternatively, or in addition, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of an antibody alters the original glycosylation pattern of the antibody. By altering is meant deleting one or more carbohydrate moieties found in the antibody, and/or adding one or more glycosylation sites that are not present in the antibody.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain.

Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to an antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to modify the antibodies used in the invention to improve effector function, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of an antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176: 1191-1195 (1992) and Shopes, B. J limmunol 148: 2918-2922 (1992).

Homodimeric antibodies with enhanced anti-tumor activity may also be prepared using heterobifunctional cross-linkers as described in Wolff et al. Cancer Research 53: 2560-2565 (1993). Alternatively, an antibody can be engineered which has dual Fc regions and may thereby have enhanced complement lysis and ADCC capabilities. See Stevenson et al. Anti-Cancer Drug Design 3: 2 19-230 (1989).

To increase the serum half life of an antibody, one may incorporate a salvage receptor binding epitope into the antibody (especially an antibody fragment) as described in U.S. Pat. No. 5,739,277, for example. As used herein, the term- "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Accumulation Ability of Antibody to Tumor Cells In Vivo

Some antibodies have high accumulation ability to tumor cells in vivo, but some antibodies don't have this ability. One of reasons of this ability may be the stability of antibody in the body. The accumulation ability to tumor cells is important for utilizing the antibody as the pharmaceutical composition. So, in vivo antibody accumulation is performed in the animal facility in accordance with institutional guidelines. In one embodiment, the mouse (e.g. BALB/cA Jcl-nu mouse) is injected subcutaneously (s.c.) with tumor cells expressing cancer marker (e.g. DKK1), in suitable buffer, in the flanks. For biodistribution studies, the mouse with fully established tumors is given radioisotope-labeled antibody via tail vein. The radioactivity for tissues of the mouse is measured.

In the case of increase of the radioactivity for tumor cells in spite of decrease of the radioactivity for the tissues like as blood, liver, kidney, intestine, spleen, pancreas, lung, heart, stomach and muscle decreases as time goes on, the antibody have high accumulation activity.

Pharmaceutical Formulations

Therapeutic formulations of an anti-DKK1 antibody used in accordance with the present invention may be prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; anti-oxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Lyophilized formulations adapted for subcutaneous administration are described in WO97/04801. Such lyophilized formulations may be reconstituted with a suitable diluent to a high protein concentration and the reconstituted formulation may be administered subcutaneously to the mammal to be treated herein.

The formulation herein may also contain more than one active compound as necessary for the particular indication being treated, preferably those with complementary activities that do not adversely affect each other. For example, it may be desirable to further provide a chemotherapeutic agent, cytokine or immunosuppressive agent. The effective amount of such other agents depends on the amount of antibody present in the formulation, the type of disease or disorder or treatment, and other factors discussed above. These are generally used in the same dosages and with administration routes as used hereinbefore or about from 1 to 99% of the heretofore employed dosages.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained release preparations include semipermeable matrices of solid hydrophobic polymers containing the agent, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non degradable ethylene-vinyl acetate, degradable lactic acid-glycolic acid copolymers such as the LUPRON DEPOT (injectable microspheres composed of lactic acid-glycolic acid copolymer and leuprolide acetate), and poly-D(−)-3-hydroxbutyric acid. The formulations to be used for in vivo administration must be sterile. This is readily accomplished by filtration through sterile filtration membranes.

Treatment with an Antibody

A composition comprising an anti-DKK1 antibody may be formulated, dosed, and administered in a fashion consistent with good medical practice. Preferably, the anti-DKK1 antibody will be a human, chimeric or humanized anti-DKK1 antibody scFv, or antibody fragment.

In the present invention, any antibodies or fragment comprising antigen binding region thereof may be used for treating or preventing cancers expressing DKK1, as long as the antibodies can binds to DKK1. In a preferred embodiment, the antibody having DKK1-neutralizing activity can be used for the treating cancers. Therefore, antibodies that may neutralize at least one function or activity of DKK1 can be used for the present invention. For example, in the present invention, function to be neutralized shown below.

promoting or enhancing cell proliferation
promoting or enhancing cancer invasion
promoting or enhancing cancer migration In order for obtaining such antibodies, many methods well known by a person skilled in the art can be used. For example, in the present invention, an antibody or fragment thereof suppressing or inhibiting cell proliferation can be obtained by contacting a candidate antibody with tumor cell in which DKK1 is over-expressed and/or up-regulated, and selecting an antibody that suppresses or inhibits the cell proliferation, comparing with that detected in the absence of the candidate antibody.

Alternatively, such antibody can also be obtained by contacting a candidate antibody with tumor cell in which DKK1 is over-expressed and/or up-regulated, and selecting an antibody that suppresses or inhibits the cell invasion or migration of the tumor cell, comparing with that detected in the absence of the candidate antibody. Method for evaluating an ability of cell invasion or migration of tumor cells is well known by a person skilled in the art (e.g. matrigel invasion assays).

According to the present invention, a pharmaceutical composition for treating a cancer characterized by either or both of the over-expression and up-regulation of DKK1 that comprises at least one of antibody or antibody fragment that specifically binds DKK1 and a pharmaceutical acceptable carrier is provided. The present invention also provides a pharmaceutical composition for inhibiting metastasis of a cancer characterized by either or both of the over-expression and up-regulation of DKK1 that comprises at least one of antibody or antibody fragment that specifically binds DKK1 and a pharmaceutical acceptable carrier. Alternatively, the present invention further provides a pharmaceutical composition for inhibiting invasion or migration of a cancer characterized by either or both of the over-expression and up-regulation of DKK1 that comprises at least one of antibody or antibody fragment that specifically binds DKK1 and a pharmaceutical acceptable carrier.

In another embodiment, the present invention also provides the use of at least one of antibody or antibody fragment that specifically binds DKK1 in manufacturing a pharmaceutical composition for treating a cancer characterized by either or both of the over-expression and up-regulation of DKK1. The present invention also provides the use of at least one of antibody or antibody fragment that specifically binds DKK1 in manufacturing a pharmaceutical composition for inhibiting metastasis of a cancer characterized by either or both of the over-expression and up-regulation of DKK1. Alternatively, the present invention further provides the use of at least one of antibody or antibody fragment that specifically binds DKK1 in manufacturing a pharmaceutical composition for inhibiting invasion or migration of a cancer characterized by either or both of the over-expression and up-regulation of DKK1.

Alternatively, the present invention further provides a method or process for manufacturing a pharmaceutical composition for treating a cancer characterized by either or both of the over-expression and up-regulation of DKK1, wherein the method or process comprises step for formulating a pharmaceutically or physiologically acceptable carrier with at least one of antibody or antibody fragment that specifically binds DKK1. The present invention also provides a method or process for manufacturing a pharmaceutical composition for inhibiting metastasis of a cancer characterized by either or both of the over-expression and up-regulation of DKK1, wherein the method or process comprises step for formulating a pharmaceutically or physiologically acceptable carrier with at least one of antibody or antibody fragment that specifically binds DKK1. Alternatively, the present invention further provides a method or process for manufacturing a pharmaceutical composition for inhibiting invasion or migration of a cancer characterized by either or both of the over-expression and up-regulation of DKK1, wherein the method or process comprises step for formulating a pharmaceutically or physiologically acceptable carrier with at least one of antibody or antibody fragment that specifically binds DKK1.

In another embodiment, the present invention also provides a method or process for manufacturing a pharmaceutical composition for treating a cancer characterized by either or both of the over-expression and up-regulation of DKK1, wherein the method or process comprises step for admixing at least one of antibody or antibody fragment that specifically binds DKK1 as an active ingredient with a pharmaceutically or physiologically acceptable carrier. The present invention also provides a method or process for manufacturing a pharmaceutical composition for inhibiting metastasis of a cancer characterized by either or both of the over-expression and up-regulation of DKK1, wherein the method or process comprises step for admixing an at least one of antibody or antibody fragment that specifically binds DKK1 with a pharmaceutically or physiologically acceptable carrier. Alternatively, the present invention further provides a method or process for manufacturing a pharmaceutical composition for inhibiting invasion or migration of a cancer characterized by either or both of the over-expression and up-regulation of DKK1, wherein the method or process comprises step for admixing an at least one of antibody or antibody fragment that specifically binds DKK1 with a pharmaceutically or physiologically acceptable carrier.

According to the present invention, any cancer characterized by either or both of the over-expression and up-regulation of DKK1 can be treated. For instance, as previously described above, DKK1 is over-expressed in various cancers including pancreatic cancer, gastric cancer, liver cancer, prostate cancer, breast cancer, bile duct cancer, cervical cancer, lung cancer and esophageal cancer. Therefore, in preferred embodiments, such cancers can be treated according to the present invention.

In the present invention, an antibody that "specifically binds to" or is "specific for" DKK1 is one that binds to DKK1 or epitope thereon without substantially binding to any other polypeptide or polypeptide epitope. In some embodiments, the extent of binding of the antibody to a protein other than DKK1 will be less than about 20%, preferably 10%, more preferably 5% of the binding of the antibody to DKK1. Those skilled in the art can evaluate or determine the binding specificity of an antibody for a polypeptide of interest using a conventional method including ELISA or radioimmunoassay (RIA). With regard to the binding of an antibody to DKK1, the term "specific binding" or "specifically binds to" or is "specific for" DKK1 means binding that is measurably different or distinct from a non-specific interaction. For example, when a binding between an antibody and protein other than DKK1 which generally is a molecule of similar structure can not substantially be detected, under the condition same as suitable one for detecting the binding between the antibody and DKK1, such antibody is specifically binds to DKK1. In preferred embodiments, where binding level between the antibody and the protein other than DKK1 is regarded as same as or comparable to background level of the assay, the antibody does not substantially binds to the protein other than DKK1.

Alternatively, specific binding can also be measured, for example, by determining binding of DKK1 compared to binding of a control molecule, which generally is a molecule of similar structure that does not have binding activity. For example, specific binding can be determined by competition with a control molecule that is similar to the DKK1, for example, an excess of non-labeled target. In this case, specific binding is indicated if the binding between the labeled DKK1 and an antibody is not competitively inhibited by excess of control molecule.

Factors for consideration in this context include the particular cancer being treated, the particular mammal being treated, the clinical condition of the individual patient, the cause of the disease or disorder, the site of delivery of the agent, the method of administration, the scheduling of administration, and other factors known to medical practitioners. The therapeutically effective amount of the antibody to be administered will be governed by such considerations.

As a general proposition, the therapeutically effective amount of the antibody administered parenterally per dose will be in the range of about 0.1 to 20 mg/kg of patient body weight per day, with the typical initial range of antibody used being in the range of about 2 to 10 mg/kg.

As noted above, however, these suggested amounts of antibody are subject to a great deal of therapeutic discretion. The key factor in selecting an appropriate dose and scheduling is the result obtained, as indicated above.

For example, relatively higher doses may be needed initially for the treatment of ongoing and acute diseases. To obtain the most efficacious results, depending on the disease or disorder, the antibody may be administered as close to the first sign, diagnosis, appearance, or occurrence of the disease or disorder as possible or during remissions of the disease or disorder.

The antibody may be administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration.

In addition, the antibody may suitably be administered by pulse infusion, e.g., with declining doses of the antibody. Preferably the dosing is given by injections, most preferably intravenous or subcutaneous injections, depending in part on whether the administration is brief or chronic.

One additionally may administer other compounds, such as cytotoxic agents, chemotherapeutic agents, immunosuppressive agents and/or cytokines with the antibody herein. The combined administration includes co-administration, using separate formulations or a single pharmaceutical formulation, and consecutive administration in either order, wherein preferably there is a time period while both (or all) active agents simultaneously exert their biological activities.

Aside from administration of the antibody to the patient, the present invention contemplates administration of the antibody by gene therapy. Such administration of a nucleic acid encoding an antibody is encompassed by the expression "administering a therapeutically effective amount of an antibody". See, for example, WO96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g. U.S. Pat. Nos. 4,892,538 and 5,283,187). There are a variety of techniques available for introducing nucleic acids into viable cells. The techniques vary depending upon whether the nucleic acid is transferred into cultured cells in vitro or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, or adeno-associated virus) and lipid-based systems (useful lipids for lipid mediated transfer of the gene are DOTMA, DOPE and DC-Choi, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., J. Biol. Chem. 262: 4429-4432 (1987); and Wagner et al, Proc. Nad. Acad. Sci. USA 87:3410-3414 (1990). For review of the currently known gene marking and gene therapy protocols see Anderson et al., Science 256: 808-813 (1992). See also WO 93/25673 and the references cited therein.

Method for Diagnosing Cancer or a Predisposition for Developing Cancer

By measuring the level of DKK1 in a subject-derived biological sample, the occurrence of cancer or a predisposition to develop cancer in a subject can be determined. Preferably, cancer is pancreatic cancer, gastric cancer, liver cancer, prostate cancer, breast cancer, bile duct cancer, cervical cancer, lung cancer and esophageal cancer. Accordingly, the present invention involves determining (e.g., measuring) the level of DKK1 in a biological sample.

According to the present invention, an intermediate result for examining the condition of a subject may also be provided. Such intermediate result may be combined with additional information to assist a doctor, nurse, or other practitioner to diagnose that a subject suffers from the disease. That is, the present invention provides a diagnostic marker DKK1 for examining cancer. Alternatively, the present invention may be used to detect cancerous cells in a subject-derived tissue, and provide a doctor with useful information to diagnose that the subject suffers from the disease.

Any biological materials may be used as the biological sample for determining the level of DKK1 so long as either the DKK1 gene or the DKK1 protein can be detected in the sample. Preferably, the biological sample includes blood, serum or other bodily fluids such as sputum. The preferred biological sample is blood or blood derived sample. The blood derived sample includes serum, plasma, or whole blood.

The subject to be diagnosed for cancer according to the methods of the present invention is preferably a mammal, examples of which include, but are not limited to, human, non-human primate, mouse, rat, dog, cat, horse and cow.

In one embodiment of the present invention, a gene transcript of the DKK1 gene is detected by measuring the amount of mRNA. For example, sequences corresponding to DKK1 gene can be used to construct probes for detecting DKK1 mRNAs by, e.g., Northern blot hybridization analysis. The hybridization of the probe to a gene transcript in a subject biological sample can be also carried out on a DNA array. As another example, the DKK1 sequence can be used to construct primers for specifically amplifying the DKK1 polynucleotide in, e.g., amplification-based detection methods such as reverse-transcription based polymerase chain reaction (RT-PCR).

In an alternate embodiment, the level of DKK1 is determined by measuring the quantity of DKK1 protein in a biological sample. A method for determining the quantity of the DKK1 protein in a biological sample includes immunoassay methods. In a preferred embodiment, the immunoassay is an ELISA.

The DKK1 level in the biological sample is then compared with a DKK1 level associated with a reference sample, such as a normal control sample. The phrase "normal control level" refers to the level of DKK1 typically found in a biological sample of a population not suffering from cancer. The reference sample is preferably of a similar nature to that of the test sample. For example, if the test sample is patient serum, the reference sample should also be serum. The DKK1 level in the biological samples from control and test subjects may be determined at the same time or, alternatively, the normal control level may be determined by a statistical method based on the results obtained by analyzing the level of DKK1 in samples previously collected from a control group.

The present inventors previously established an ELISA system to measure serum levels of DKK1 and found that serum DKK1 levels were significantly higher in lung and esophageal cancer patients than in healthy controls (WO2007/013671). In the present invention, the serum DKK1 levels in pancreatic cancer, gastric cancer, liver cancer, prostate cancer, breast cancer, bile duct cancer, cervical cancer, lung cancer and esophageal cancer patients are disclosed which also significantly higher levels than in healthy controls.

In the present invention, the standard value of the blood concentration of DKK1 can be determined statistically. For example, the blood concentration of DKK1 in healthy individuals can be measured to determine the standard blood concentration of DKK1 statistically. When a statistically sufficient population is gathered, a value in the range of twice or three times the standard deviation (S.D.) from the mean value is often used as the standard value. Therefore, values corresponding to the mean value+2×S.D. or mean value+3×S.D. may be used as standard values. The standard values set as described theoretically include 90% and 99.7% of healthy individuals, respectively.

Alternatively, standard values can also be set based on the actual blood concentration of DKK1 in cancer patients. Generally, standard values set this way minimize the percentage of false positives, and are selected from a range of values satisfying conditions that can maximize detection sensitivity. Herein, the percentage of false positives refers to a percentage, among healthy individuals, of patients whose blood concentration of DKK1 is judged to be higher than a standard value. On the contrary, the percentage, among healthy individuals, of patients whose blood concentration of DKK1 is judged to be lower than a standard value indicates specificity. That is, the sum of the false positive percentage and the specificity is always 1. The detection sensitivity refers to the percentage of patients whose blood concentration of DKK1 is judged to be higher than a standard value, among all cancer patients within a population of individuals for whom the presence of cancer has been determined.

Furthermore, in the context of the present invention, the percentage of cancer patients among patients whose DKK1 concentration was judged to be higher than a standard value represents the positive predictive value. On the other hand, the percentage of healthy individuals among patients whose DKK1 concentration was judged to be lower than a standard value represents the negative predictive value. The relationship between these values is summarized in Table 1. As the relationship shown below indicates, each of the values for sensitivity, specificity, positive predictive value, and negative predictive value, which are indexes for evaluating the diagnostic accuracy for cancer, varies depending on the standard value for judging the level of the blood concentration of DKK1.

TABLE 11

| Blood concentration of DKK1 | Cancer patients | Healthy individuals | |
|---|---|---|---|
| High | a: True positive | b: False positive | Positive predictive value a/(a + b) |
| Low | c: False negative | d: True negative | Negative predictive value d/(c + d) |
| | Sensitivity a/(a + c) | Specificity d/(b + d) | |

As mentioned previously, a standard value is usually set such that the false positive ratio is low and the sensitivity is high. However, as is also apparent from the relationship shown above, there is a trade-off between the false positive ratio and sensitivity. That is, if the standard value is decreased, the detection sensitivity increases. However, since the false positive ratio also increases, it is difficult to satisfy the conditions to have a "low false positive ratio". Considering this situation, for example, values that give the following predicted results may be selected as the preferable standard values in the present invention.

Standard values for which the false positive ratio is 50% or less (that is, standard values for which the specificity is not less than 50%).

Standard values for which the sensitivity is not less than 20%.

In the context of the present invention, the standard values can be set using a receiver operating characteristic (ROC) curve. A ROC curve is a graph that shows the detection sensitivity on the vertical axis and the false positive ratio (that is, "1-specificity") on the horizontal axis. In the present invention, an ROC curve can be obtained by plotting the changes in the sensitivity and the false positive ratio, which were obtained after continuously varying the standard value for determining the high/low degree of the blood concentration of DKK1.

The "standard value" for obtaining the ROC curve is a value temporarily used for the statistical analyses. The "standard value" for obtaining the ROC curve can generally be continuously varied within a range that is allowed to cover all selectable standard values. For example, the standard value can be varied between the smallest and largest measured DKK1 values in an analyzed population.

Based on the obtained ROC curve, a preferable standard value to be used in the present invention can be selected from a range that satisfies the above-mentioned conditions. Alternatively, a standard value can be selected based on an ROC curve produced by varying the standard values from a range that encompasses most of the measured DKK1 values.

DKK1 in the blood can be measured by any method that can quantitate proteins. For example, immunoassay, liquid chromatography, surface plasmon resonance (SPR), mass spectrometry, or the like can be used in connection with the present invention. In mass spectrometry, proteins can be quantitated by using a suitable internal standard. For example, isotope-labeled DKK1 can be used as the internal standard. The concentration of DKK1 in the blood can be determined from the peak intensity of DKK1 in the blood and that of the internal standard. Generally, the matrix-assisted laser desorption/ionization (MALDI) method is used for mass spectrometry of proteins. With an analysis method that uses mass spectrometry or liquid chromatography, DKK1 can also be analyzed simultaneously with other tumor markers (e.g. CEA or pro-GRP).

A preferable method for measuring DKK1 in the present invention is the immunoassay. The amino acid sequence of DKK1 is known (Genbank Accession Number AY359005). The amino acid sequence of DKK1 is shown in SEQ ID NO: 2, and the nucleotide sequence of the cDNA encoding it is shown in SEQ ID NO: 1. Therefore, those skilled in the art can prepare antibodies by synthesizing necessary immunogens based on the amino acid sequence of DKK1. The peptide used as immunogen can be easily synthesized using a peptide synthesizer. The synthetic peptide can be used as an immunogen by linking it to a carrier protein.

Keyhole limpet hemocyanin, myoglobin, albumin, and the like can be used as the carrier protein. Preferable carrier proteins are KLH, bovine serum albumin, and such. The maleimidobenzoyl-N-hydroxysuccinimide ester method (hereinafter abbreviated as the MBS method) and the like are generally used to link synthetic peptides to carrier proteins.

Specifically, a cysteine is introduced into the synthetic peptide and the peptide is crosslinked to KLH by MBS using the cysteine's SH group. The cysteine residue may be introduced at the N-terminus or C-terminus of the synthesized peptide.

Alternatively, DKK1 can be prepared using the nucleotide sequence of DKK1, or a portion thereof. DNAs including the necessary nucleotide sequence can be cloned using mRNAs prepared from DKK1-expressing tissues. Alternatively, commercially available cDNA libraries can be used as the cloning source. The obtained genetic recombinants of DKK1, or fragments thereof, can also be used as the immunogen. DKK1 recombinants expressed in this manner are preferable as the immunogen for obtaining the antibodies used in the present invention. The method of obtaining the anti-DKK1 antibody is referred above.

When antibodies against DKK1 contact DKK1, the antibodies bind to the antigenic determinant (epitope) that the antibodies recognize through an antigen-antibody reaction. The binding of antibodies to antigens can be detected by various immunoassay principles. Immunoassays can be broadly categorized into heterogeneous analysis methods and homogeneous analysis methods. To maintain the sensitivity and specificity of immunoassays to a high level, the use of monoclonal antibodies is desirable. Methods of the present invention for measuring DKK1 by various immunoassay formats are specifically explained.

First, methods for measuring DKK1 using a heterogeneous immunoassay are described. In heterogeneous immunoassays, a mechanism for detecting antibodies that bind to DKK1 after separating them from those that do not bind to DKK1 is required.

To facilitate the separation, immobilized reagents are generally used. For example, a solid phase onto which antibodies recognizing DKK1 have been immobilized is first prepared (immobilized antibodies). DKK1 is made to bind to these, and secondary antibodies are further reacted thereto.

When the solid phase is separated from the liquid phase and further washed, as necessary, secondary antibodies remain on the solid phase in proportion to the concentration of DKK1. By labeling the secondary antibodies, DKK1 can be quantitated by measuring the signal derived from the label.

Any method may be used to bind the antibodies to the solid phase. For example, antibodies can be physically adsorbed to hydrophobic materials such as polystyrene. Alternatively, antibodies can be chemically bound to a variety of materials having functional groups on their surfaces. Furthermore, antibodies labeled with a binding ligand can be bound to a solid phase by trapping them using a binding partner of the ligand. Combinations of a binding ligand and its binding partner include avidin-biotin and such. The solid phase and antibodies can be conjugated at the same time or before the reaction between the primary antibodies and DKK1.

Similarly, the secondary antibodies do not need to be directly labeled. That is, they can be indirectly labeled using antibodies against antibodies or using binding reactions such as that of avidin-biotin.

The concentration of DKK1 in a sample is determined based on the signal intensities obtained using standard samples with known DKK1 concentrations.

Any antibody can be used as the immobilized antibody and secondary antibody for the heterogeneous immunoassays mentioned above, so long as it is an antibody, or a fragment including an antigen-binding site thereof, that recognizes DKK1. Therefore, it may be a monoclonal antibody, a polyclonal antibody, or a mixture or combination of both. For example, a combination of monoclonal antibodies and polyclonal antibodies is a preferable combination in the present invention. Alternatively, when both antibodies are monoclonal antibodies, combining monoclonal antibodies recognizing different epitopes is preferable.

Since the antigens to be measured are sandwiched by antibodies, such heterogeneous immunoassays are called sandwich methods. Since sandwich methods excel in the measurement sensitivity and the reproducibility, they are a preferable measurement principle in the present invention.

The principle of competitive inhibition reactions can also be applied to the heterogeneous immunoassays. Specifically, they are immunoassays based on the phenomenon where DKK1 in a sample competitively inhibits the binding between DKK1 with a known concentration and an antibody. The concentration of DKK1 in the sample can be determined by labeling DKK1 with a known concentration and measuring the amount of DKK1 that reacted (or did not react) with the antibody.

A competitive reaction system is established when antigens with a known concentration and antigens in a sample are simultaneously reacted to an antibody. Furthermore, analyses by an inhibitory reaction system are possible when antibodies are reacted with antigens in a sample, and antigens with a known concentration are reacted thereafter. In both types of reaction systems, reaction systems that excel in the operability can be constructed by setting either one of the antigens with a known concentration used as a reagent component or the antibody as the labeled component, and the other one as the immobilized reagent.

Radioisotopes, fluorescent substances, luminescent substances, substances having an enzymatic activity, macroscopically observable substances, magnetically observable substances, and such are used in these heterogeneous immunoassays. Specific examples of these labeling substances are shown below.

Examples of substances having an enzymatic activity include, but are not limited to:
peroxidase,
alkaline phosphatase,
urease, catalase,
glucose oxidase,
lactate dehydrogenase, or
amylase, etc.

Examples of fluorescent substances include, but are not limited to:
fluorescein isothiocyanate,
tetramethylrhodamine isothiocyanate,
substituted rhodamine isothiocyanate, or
dichlorotriazine isothiocyanate, etc.

Examples of radioisotopes include, but are not limited to:
tritium,
$^{125}$I, or
$^{131}$I, etc.

Among these, non-radioactive labels such as enzymes are an advantageous label in terms of safety, operability, sensitivity, and such. Enzymatic labels can be linked to antibodies or to DKK1 by known methods such as the periodic acid method or maleimide method.

As the solid phase, beads, inner walls of a container, fine particles, porous carriers, magnetic particles, or such are used. Solid phases formed using materials such as polystyrene, polycarbonate, polyvinyltoluene, polypropylene, polyethylene, polyvinyl chloride, nylon, polymethacrylate, latex, gelatin, agarose, glass, metal, ceramic, or such can be used. Solid materials in which functional groups to chemically bind antibodies and such have been introduced onto the surface of the above solid materials are also known. Known binding methods, including chemical binding such as poly-L-lysine or glutaraldehyde treatment and physical adsorption, can be applied for solid phases and antibodies (or antigens).

Although the steps of separating the solid phase from the liquid phase and the washing steps are required in all heterogeneous immunoassays exemplified herein, these steps can easily be performed using the immunochromatography method, which is a variation of the sandwich method.

Specifically, antibodies to be immobilized are immobilized onto porous carriers capable of transporting a sample solution by the capillary phenomenon, then a mixture of a sample containing DKK1 and labeled antibodies is deployed therein by this capillary phenomenon. During deployment, DKK1 reacts with the labeled antibodies, and when it further contacts the immobilized antibodies, it is trapped at that location. The labeled antibodies that do not react with DKK1 pass through, without being trapped by the immobilized antibodies.

As a result, the presence of DKK1 can be detected using, as an index, the signals of the labeled antibodies that remain at the location of the immobilized antibodies. If the labeled antibodies are maintained upstream in the porous carrier in advance, all reactions can be initiated and completed by just dripping in the sample solutions, and an extremely simple reaction system can be constructed. In the immunochromatography method, labeled components that can be distinguished macroscopically, such as colored particles, can be combined to construct an analytical device that does not even require a special reader.

Furthermore, in the conventional immunochromatography method, the detection sensitivity for DKK1 can be adjusted. For example, by adjusting the detection sensitivity near the cutoff value described below, the aforementioned labeled components can be detected when the cutoff value is exceeded. By using such a device, whether a subject is positive or negative can be judged very simply. By adopting a constitution that allows a macroscopic distinction of the labels, necessary examination results can be obtained by simply applying blood samples to the device for immunochromatography.

Various methods for adjusting the detection sensitivity of the immunochromatography method are known. For example, a second immobilized antibody for adjusting the detection sensitivity can be placed between the position where samples are applied and the immobilized antibodies (Japanese Patent Application Kokai Publication No. (JP-A) H06-341989 (unexamined, published Japanese patent application)). DKK1 in the sample is trapped by the second immobilized antibody while deploying from the position where the sample was applied to the position of the first immobilized antibody for label detection. After the second immobilized antibody is saturated, DKK1 can reach the position of the first immobilized antibody located downstream. As a result, when the concentration of DKK1 in the sample exceeds a predetermined concentration, DKK1 bound to the labeled antibody is detected at the position of the first immobilized antibody.

Next, homogeneous immunoassays are explained. As opposed to heterogeneous immunological assay methods that require a separation of the reaction solutions as described above, DKK1 can also be measured using homogeneous analysis methods. Homogeneous analysis methods allow the detection of antigen-antibody reaction products without their separation from the reaction solutions.

A representative homogeneous analysis method is the immunoprecipitation reaction, in which antigenic substances are quantitatively analyzed by examining precipitates produced following an antigen-antibody reaction. Polyclonal antibodies are generally used for the immunoprecipitation reactions. When monoclonal antibodies are applied, multiple types of monoclonal antibodies that bind to different epitopes of DKK1 are preferably used. The products of precipitation reactions that follow the immunological reactions can be macroscopically observed or can be optically measured for conversion into numerical data.

The immunological particle agglutination reaction, which uses as an index the agglutination by antigens of antibody-sensitized fine particles, is a common homogeneous analysis method. As in the aforementioned immunoprecipitation reaction, polyclonal antibodies or a combination of multiple types of monoclonal antibodies can be used in this method as well.

Fine particles can be sensitized with antibodies through sensitization with a mixture of antibodies, or they can be prepared by mixing particles sensitized separately with each antibody. Fine particles obtained in this manner gives matrix-like reaction products upon contact with DKK1. The reaction products can be detected as particle aggregation. Particle aggregation may be macroscopically observed or can be optically measured for conversion into numerical data.

Immunological analysis methods based on energy transfer and enzyme channeling are known as homogeneous immunoassays. In methods utilizing energy transfer, different optical labels having a donor/acceptor relationship are linked to multiple antibodies that recognize adjacent epitopes on an antigen. When an immunological reaction takes place, the two parts approach and an energy transfer phenomenon occurs, resulting in a signal such as quenching or a change in the fluorescence wavelength. On the other hand, enzyme channeling utilizes labels for multiple antibodies that bind to adjacent epitopes, in which the labels are a combination of enzymes having a relationship such that the reaction product of one enzyme is the substrate of another. When the two parts approach due to an immunological reaction, the enzyme reactions are promoted; therefore, their binding can be detected as a change in the enzyme reaction rate.

In the present invention, blood for measuring DKK1 can be prepared from blood drawn from patients. Preferable blood samples are the serum or plasma. Serum or plasma samples can be diluted before the measurements. Alternatively, the whole blood can be measured as a sample and the obtained measured value can be corrected to determine the serum concentration. For example, concentration in whole blood can be corrected to the serum concentration by determining the percentage of corpuscular volume in the same blood sample.

In a preferred embodiment, the immunoassay is an ELISA. The present inventors established sandwich ELISA to detect serum DKK1 in patients with cancer.

The DKK1 level in the blood sample is then compared with a DKK1 level associated with a reference sample, such as a normal control sample or other known sample (e.g., a reference cancer sample). The phrase "normal control level" refers to the level of DKK1 typically found in a blood sample of a population not suffering from cancer. The reference sample is preferably of a similar nature to that of the test sample. For example, if the test samples are patient serum, the reference sample should also be serum. The DKK1 level in the blood samples from control and test subjects may be determined at the same time or, alternatively, the normal control level may be determined by a statistical method based on the results obtained by analyzing the level of DKK1 in samples previously collected from a control group.

The DKK1 level may also be used to monitor the course of treatment of cancer. In this method, a test blood sample is provided from a subject undergoing treatment for cancer. Preferably, multiple test blood samples are obtained from the subject at various time points before, during, or after the treatment. The level of DKK1 in the post-treatment sample may then be compared with the level of DKK1 in the pre-treatment sample or, alternatively, with a reference sample (e.g., a normal control level or known reference level). For example, if the post-treatment DKK1 level is lower than the pre-treatment DKK1 level, one can conclude that the treatment was efficacious. Likewise, if the post-treatment DKK1 level is similar to the normal control DKK1 level, one can also conclude that the treatment was efficacious.

An "efficacious" treatment is one that leads to a reduction in the level of DKK1 or a decrease in size, prevalence, or metastatic potential of cancer in a subject. When a treatment is applied prophylactically, "efficacious" means that the treatment retards or prevents occurrence of cancer or alleviates a clinical symptom of cancer. The assessment of cancer can be made using standard clinical protocols. Furthermore, the efficaciousness of a treatment can be determined in association with any known method for diagnosing or treating cancer. For example, cancer is routinely diagnosed histopathologically or by identifying symptomatic anomalies.

Method for Predicting a Cancer or a Predisposition for Developing Cancer, a Cancer Metastasis, a Cancer Invasion or a Cancer Cell Migration in a Subject According to the present invention, it was shown that the higher the expression level of the DKK1 gene measured in metastatic or invasive cancer. The present invention provides a method for predicting a cancer or a predisposition for developing cancer, a cancer metastasis, a cancer invasion or a cancer cell migration in a subject, in particular pancreatic cancer, gastric cancer, liver cancer, prostate cancer, breast cancer, bile duct cancer cervical cancer, lung cancer, and esophageal cancer by detecting the expression level of the DKK1 gene in a biological sample of the patient; comparing the detected expression level to a control level; and correlating an increased expression level to the control level with an indication of developing cancer, a cancer metastasis, a cancer invasion or a cancer cell migration.

According to the present invention, an intermediate result for examining the condition of a subject may also be provided. Such intermediate result may be combined with additional information to assist a doctor, nurse, or other practitioner to diagnose that a subject's cancer set up the metastasis or invasion. That is, the present invention provides a diagnostic marker DKK1 for predicting a cancer, metastasis or invasion thereof. Alternatively, the present invention may be used to assess the malignancy in a cancer subject.

According to the present method the present invention, the term "metastasis" is used as the spread of a disease from one organ or part to another non-adjacent organ or part. Especially, cancer cells from primary tumor enter lymphatic and blood vessels, circulate through the bloodstream, and settle down to grow within normal tissues elsewhere in the body. In the present invention, the term "cancer invasion" refer to the phenomenon which the cancer cells break into the surrounding tissue and expand the lesion.

Preferably, the present invention provides a method for predicting or assessing developing cancer, a cancer metastasis, a cancer invasion or a cancer cell migration in a subject, the method comprising the steps of:

(a) detecting an expression level of DKK1 in a specimen collected from said subject;

(b) comparing the expression level of DKK1 in said specimen to that of a metastasis, invasion, or migration positive case and metastasis, invasion, or migration negative case; and (c) wherein specimen expression level similar to that of a metastasis, invasion, or migration positive case indicates a high risk of metastasis, invasion, or migration of cancer, and wherein specimen expression level similar to that of a metastasis, invasion, or migration negative case indicates a low risk of metastasis, invasion, or migration of cancer.

Alternatively, the present invention also provides a method for determining, estimating, or evaluating either or both of migration activity and invasion activity of cancer in a subject, the method comprising the steps of:

(a) detecting an expression level of DKK1 in a specimen collected from said subject;

(b) correlating either or both of migration activity and invasion activity with the expression level detected in step a).

In the present invention, for example, migration activity or invasion activity may be correlated with the expression level of DKK1, by comparing the expression level of DKK1 in said specimen to that of a metastasis, invasion, or migration positive case and metastasis, invasion, or migration negative case. When, the expression level in the specimen similar to that of a metastasis, invasion, or migration positive case indicates a high activity of metastasis, invasion, or migration of cancer. Alternatively, expression level of the specimen similar to that of a metastasis, invasion, or migration negative case indicates a low activity of metastasis, invasion, or migration of cancer. Furthermore, migration activity or invasion activity may also be correlated with the expression level of DKK1, by calibrating with the expression level of DKK1 and these activities. For instance, expression levels of DKK1 of cells having a various level of these activities are determined to correlate with the expression level and such activities. Methods for evaluating a migration activity or invasion activity are well known. For example, such activities may be evaluated with matrigel invasion assay.

The patient-derived biological sample used for the method may be any sample derived from the subject to be predicted so long as the DKK1 gene can be detected in the sample. Preferably, the biological sample is an pancreatic, gastric, liver, prostate, breast, bile duct, cervical, lung or esophageal cell. Furthermore, the biological sample includes bodily fluids such as sputum, blood, serum, or plasma. Moreover, the sample may be cells isolated from a tissue. The biological samples may be obtained from a patient at various time points, including before, during, and/or after a treatment. For example, the biological samples may be obtained by a surgery, or biopsy.

According to the present method, the "control level" used for comparison may be, for example, the expression level of the DKK1 gene detected in biological samples collected from individual before any kind of treatment in the individual or a population of individuals who showed no developing cancer, a cancer metastasis, a cancer invasion or a cancer cell migration, after the treatment ("metastasis, invasion, or migration negative case"). Alternatively, the "control level" may be the expression level of the DKK1 gene detected before any kind of treatment in an individual or a population of individuals who showed the activation of developing cancer, a cancer metastasis, a cancer invasion or a cancer cell migration, after the treatment ("metastasis, invasion, or migration positive case"). Alternatively, when biological samples were collected during a treatment e.g. surgery, "control level" may also be obtained from such sample.

The "control level" is a single expression pattern derived from a single reference population or from a plurality of expression patterns. Preferably, cancer is pancreatic cancer, gastric cancer, liver cancer, prostate cancer, breast cancer, bile duct cancer cervical cancer, lung cancer or esophageal cancer. It is preferable to use the standard value of the expression levels of the DKK1 gene in a patient group with a known disease state. The standard value may be obtained by any method known in the art. For example, a range of mean+/−2 S.D. or mean+/−3 S.D. may be used as standard value.

The control level may be determined at the same time with the test biological sample by using a sample(s) previously collected and stored before any kind of treatment from cancer patient(s) (control or control group) whose disease ("positive, or negative case") state are known.

Alternatively, the control level may be determined by a statistical method based on the results obtained by analyzing the expression level of the DKK1 gene in samples previously collected and stored from a control group. Furthermore, the control level can be a database of expression patterns obtained from previously tested cells. Moreover, according to an aspect of the present invention, the expression level of the DKK1 gene in a biological sample may be compared to multiple control levels, which control levels are determined from multiple reference samples. It is preferred to use a control level determined from a reference sample derived from a tissue type similar to that of the patient-derived biological sample.

An expression level of the DKK1 gene in a biological sample can be considered altered when the expression level differs from the control level by more than 1.0, 1.5, 2.0, 5.0, 10.0, or more fold. Alternatively, an expression level of the DKK1 gene in a biological sample can be considered altered, when the expression level is increased or decreased to the control level at least 10%, 20%, 30%, 40%, 50%, 60%, 80%, 90%, or more.

The difference in the expression level between the test biological sample and the control level can be normalized to a control, e.g., housekeeping gene. For example, polynucleotides whose expression levels are known not to differ between the cancerous and non-cancerous cells, including those coding for beta-actin, glyceraldehyde 3-phosphate dehydrogenase, and ribosomal protein PI, may be used to normalize the expression levels of the DKK1 gene.

The expression level may be determined by detecting the gene transcript in the patient-derived biological sample using techniques well known in the art. The gene transcripts detected by the present method include both the transcription and translation products, such as mRNA and protein.

For instance, the transcription product of the DKK1 gene can be detected by hybridization, e.g., Northern blot hybridization analyses, that use an DKK1 gene probe to the gene transcript. The detection may be carried out on a chip or an array. The use of an array is preferable for detecting the expression level of a plurality of genes including the DKK1 gene. As another example, amplification-based detection methods, such as reverse-transcription based polymerase chain reaction (RT-PCR) which use primers specific to the DKK1 gene may be employed for the detection. The DKK1 gene-specific probe or primers may be designed and prepared using conventional techniques by referring to the whole sequence of the DKK1 gene.

Specifically, a probe or primer used for the present method hybridizes under stringent, moderately stringent, or low stringent conditions to the mRNA of the DKK1 gene. As used herein, the phrase "stringent (hybridization) conditions" refers to conditions under which a probe or primer will hybridize to its target sequence, but to no other sequences. Stringent conditions are sequence-dependent and will be different under different circumstances. Specific hybridization of longer sequences is observed at higher temperatures than shorter sequences. Generally, the temperature of a stringent condition is selected to be about 5 degrees C. lower than the thermal melting point (Tm) for a specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 degrees C. for short probes or primers (e.g., 10 to 50 nucleotides) and at least about 60 degrees C. for longer probes or primers. Stringent conditions may also be achieved with the addition of destabilizing agents, such as formamide.

Alternatively, the translation product may be detected for the assessment of the present invention. For example, the quantity of the DKK1 protein may be determined. A method for determining the quantity of the protein as the translation product includes immunoassay methods that use an antibody specifically recognizing the DKK1 protein. The antibody may be monoclonal or polyclonal. Furthermore, any fragment or modification (e.g., chimeric antibody, scFv, Fab, F(ab')2, Fv, etc.) of the antibody may be used for the detection, so long as the fragment retains the binding ability to the DKK1 protein. Methods to prepare these kinds of antibodies for the detection of proteins are well known in the art, and any method may be employed in the present invention to prepare such antibodies and equivalents thereof.

As another method to detect the expression level of the DKK1 gene based on its translation product, the intensity of staining may be observed via immunohistochemical analysis using an antibody against DKK1 protein. Namely, the observation of strong staining indicates an increased presence of the DKK1 protein and at the same time high expression level of the DKK1 gene.

Alternatively, the present invention provides a reagent for diagnosing a cancer or a predisposition for developing cancer, a cancer metastasis, a cancer invasion or a cancer cell migration in a subject. Preferably, the reagent of the present invention comprises;
(a) a probe or primer which hybridizes under stringent, moderately stringent, or low stringent conditions to the mRNA of the DKK1 gene, or
(b) an antibody or antibody fragment which is capable of binding to DKK1 protein or a partial peptide thereof.

As an embodiment of the present invention, when the reagent is a probe against the DKK1 mRNA, the reagent may be immobilized on a solid matrix, such as a porous strip, to form at least one detection site. The measurement or detection region of the porous strip may include a plurality of sites, each containing a nucleic acid (probe). A test strip may also contain sites for negative and/or positive controls. Alternatively, control sites may be located on a strip separated from the test strip. Optionally, the different detection sites may contain different amounts of immobilized nucleic acids, i.e., a higher amount in the first detection site and lesser amounts in subsequent sites. Upon the addition of test sample, the number of sites displaying a detectable signal provides a quantitative indication of the amount of DKK1 mRNA present in the sample. The detection sites may be configured in any suitably detectable shape and are typically in the shape of a bar or dot spanning the width of a test strip.

Serological Diagnosing Kit

Components used to carry out the diagnosis of cancer according to the present invention can be combined in advance and supplied as a testing kit. Accordingly, the present invention provides a kit for detecting a cancer, containing:
(i) an immunoassay reagent for determining a level of DKK1 in a blood sample; and
(ii) a positive control sample for DKK1.

The reagents for the immunoassays which constitute a kit of the present invention may comprise reagents necessary for the various immunoassays described above. Specifically, the reagents for the immunoassays include, for example, an antibody that recognizes the substance to be measured. The antibody can be modified depending on the assay format of the immunoassay. ELISA can be used as a preferable assay format of the present invention. In ELISA, for example, a first antibody immobilized onto a solid phase and a second antibody having a label are generally used.

Therefore, the immunoassay reagents for ELISA can include a first antibody immobilized onto a solid phase carrier. Fine particles or the inner walls of a reaction container can be used as the solid phase carrier. Magnetic particles can be used as the fine particles. Alternatively, multi-well plates such as 96-well microplates are often used as the reaction containers. Containers for processing a large number of samples, which are equipped with wells having a smaller volume than in 96-well microplates at a high density, are also known. In the present invention, the inner walls of these reaction containers can be used as the solid phase carriers.

The immunoassay reagents for ELISA may further include a second antibody having a label. The second antibody for ELISA may be an antibody onto which an enzyme is directly or indirectly linked. Methods for chemically linking an enzyme to an antibody are known. For example, immunoglobulins can be enzymatically cleaved to obtain fragments containing the variable regions. By reducing the —SS-bonds in these fragments to —SH groups, bifunctional linkers can be attached. By linking an enzyme to the bifunctional linkers in advance, enzymes can be linked to the antibody fragments. Alternatively, to indirectly link an enzyme, for example, the avidin-biotin binding can be used. That is, an enzyme can be indirectly linked to an antibody by contacting a biotinylated antibody with an enzyme to which avidin has been attached. In addition, an enzyme can be indirectly linked to a second antibody using a third antibody which is an enzyme-labeled antibody recognizing the second antibody. For example, enzymes such as those exemplified above can be used as the enzymes to label the antibodies.

Kits of the present invention may further include a positive control for DKK1. A positive control for DKK1 comprises DKK1 whose concentration has been determined in advance. Preferable concentrations are, for example, a concentration set as the standard value in a testing method of the present invention. Alternatively, a positive control having a higher concentration can also be combined. A positive control DKK1 is preferable as the positive control of the present invention.

Therefore, the present invention provides a positive control for detecting cancer, which includes DKK1 at concentrations above a normal value. Alternatively, the present invention relates to the use of a blood sample containing DKK1 at concentrations above a normal value in the production of a positive control for the detection of cancer. DKK1 an index for lung and esophageal cancer has been previously described; however, that DKK1 can serve as an index for a wide range of divergent cancers is a novel finding of the present invention.

The positive controls in the present invention are preferably in a liquid form. In the present invention, blood samples are used as samples. Therefore, samples used as controls also need to be in a liquid form. Alternatively, by dissolving a dried positive control with a predefined amount of liquid at the time of use, a control that gives the tested concentration can be prepared. By packaging, together with a dried positive control, an amount of liquid necessary to dissolve it, the user can obtain the necessary positive control by just mixing them. DKK1 used as the positive control can be a naturally-derived protein or it may be a recombinant protein. Not only positive controls, but also negative controls can be combined in the kits of the present invention. The positive controls or negative controls are used to verify that the results indicated by the immunoassays are correct.

The DKK1 level may also be used to monitor the course of treatment of cancer. In this method, a test biological sample is provided from a subject undergoing treatment for cancer. Preferably, cancer is pancreatic cancer, gastric cancer, liver cancer, prostate cancer, breast cancer, bile duct cancer cervical cancer, esophageal or lung cancer. Preferably, multiple test biological samples are obtained from the subject at various time points before, during or after the treatment. The level of DKK1 in the post-treatment sample may then be compared with the level of DKK1 in the pre-treatment sample or, alternatively, with a reference sample (e.g., a normal control level). For example, if the post-treatment DKK1 level is lower than the pre-treatment DKK1 level, one can conclude that the treatment was efficacious. Likewise, if the post-treatment DKK1 level is similar to the normal control DKK1 level, one can also conclude that the treatment was efficacious.

An "efficacious" treatment is one that leads to a reduction in the level of DKK1 or a decrease in size, prevalence or metastatic potential of cancer in a subject. When a treatment is applied prophylactically, "efficacious" means that the treatment retards or prevents occurrence of cancer or alleviates a clinical symptom of cancer. The assessment of cancer can be made using standard clinical protocols. Furthermore, the efficaciousness of a treatment can be determined in association with any known method for diagnosing or treating cancer. For example, cancer is routinely diagnosed histopathologically or by identifying symptomatic anomalies such as chronic cough, hoarseness, coughing up blood, weight loss, loss of appetite, shortness of breath, wheezing, repeated bouts of bronchitis or pneumonia and chest pain.

Moreover, the present method for diagnosing cancer may also be applied for assessing the prognosis of a patient with the cancer by comparing the level of DKK1 in a patient-derived biological sample with that of a reference sample. Preferably, cancer is pancreatic cancer, gastric cancer, liver cancer, prostate cancer, breast cancer, bile duct cancer, cervical cancer, lung cancer or esophageal cancer. Alternatively, the level of DKK1 in the biological sample may be measured over a spectrum of disease stages to assess the prognosis of the patient. An increase in the level of DKK1 as compared to a normal control level indicates less favorable prognosis. A similarity in the level of DKK1 as compared to a normal control level indicates a more favorable prognosis of the patient.

Screening for Anticancer Compound

In the context of the present invention, agents to be identified through the present screening methods may be any compound or composition including several compounds. Furthermore, the test agent exposed to a cell or protein according to the screening methods of the present invention may be a single compound or a combination of compounds. When a combination of compounds is used in the methods, the compounds may be contacted sequentially or simultaneously.

Any test agent, for example, cell extracts, cell culture supernatant, products of fermenting microorganism, extracts from marine organism, plant extracts, purified or crude proteins, peptides, non-peptide compounds, synthetic micromolecular compounds (including nucleic acid constructs, such as antisense RNA, siRNA, ribozymes, etc.) and natural compounds can be used in the screening methods of the present invention. The test agent of the present invention can be also obtained using any of the numerous approaches in combinatorial library methods known in the art, including (1) biological libraries, (2) spatially addressable parallel solid phase or solution phase libraries, (3) synthetic library methods requiring deconvolution, (4) the "one-bead one-compound" library method and (5) synthetic library methods using affinity chromatography selection. The biological library methods using affinity chromatography selection is limited to peptide libraries, while the other four approaches are applicable to peptide, non-peptide oligomer or small molecule libraries of compounds (Lam, Anticancer Drug Des 1997, 12: 145-67). Examples of methods for the synthesis of molecular libraries can be found in the art (DeWitt et al., Proc Natl Acad Sci USA 1993, 90: 6909-13; Erb et al., Proc Natl Acad Sci USA 1994, 91: 11422-6; Zuckermann et al., J Med Chem 37: 2678-85, 1994; Cho et al., Science 1993, 261: 1303-5; Carell et al., Angew Chem Int Ed Engl 1994, 33: 2059; Carell et al., Angew Chem Int Ed Engl 1994, 33: 2061; Gallop et al., J Med Chem 1994, 37: 1233-51). Libraries of compounds may be presented in solution (see Houghten, Bio/Techniques 1992, 13: 412-21) or on beads (Lam, Nature 1991, 354: 82-4), chips (Fodor, Nature 1993, 364: 555-6), bacteria (U.S. Pat. No. 5,223,409), spores (U.S. Pat. Nos. 5,571,698; 5,403,484, and 5,223,409), plasmids (Cull et al., Proc Natl Acad Sci USA 1992, 89: 1865-9) or phage (Scott and Smith, Science 1990, 249: 386-90; Devlin, Science 1990, 249: 404-6; Cwirla et al., Proc Natl Acad Sci USA 1990, 87: 6378-82; Felici, J Mol Biol 1991, 222: 301-10; US Pat. Application 2002103360).

A compound in which apart of the structure of the compound screened by any of the present screening methods is converted by addition, deletion and/or replacement, is included in the agents obtained by the screening methods of the present invention.

Furthermore, when the screened test agent is a protein, for obtaining a DNA encoding the protein, either the whole amino acid sequence of the protein may be determined to deduce the nucleic acid sequence coding for the protein, or partial amino acid sequence of the obtained protein may be analyzed to prepare an oligo DNA as a probe based on the sequence, and screen cDNA libraries with the probe to obtain a DNA encoding the protein. The obtained DNA is confirmed it's usefulness in preparing the test agent which is a candidate for treating or preventing cancer. Test agents useful in the screenings described herein can also be antibodies that specifically bind to DKK1 protein or partial peptides thereof that lack the biological activity of the original proteins in vivo. The antibodies are described in above.

Although the construction of test agent libraries is well known in the art, herein below, additional guidance in identifying test agents and construction libraries of such agents for the present screening methods are provided.

(i) Molecular Modeling:

Construction of test agent libraries is facilitated by knowledge of the molecular structure of compounds known to have the properties sought, and/or the molecular structure of the target molecules to be inhibited, i.e., DKK1. One approach to preliminary screening of test agents suitable for further evaluation is computer modeling of the interaction between the test agent and its target.

Computer modeling technology allows the visualization of the three-dimensional atomic structure of a selected molecule and the rational design of new compounds that will interact with the molecule. The three-dimensional construct typically depends on data from x-ray crystallographic analysis or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

An example of the molecular modeling system described generally above includes the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen et al. Acta Pharmaceutica Fennica 1988, 97: 159-66; Ripka, New Scientist 1988, 54-8; McKinlay & Rossmann, Annu Rev Pharmacol Toxiciol 1989, 29: 111-22; Perry & Davies, Prog Clin Biol Res 1989, 291: 189-93; Lewis & Dean, Proc R Soc Lond 1989, 236: 125-40, 141-62; and, with respect to a model receptor for nucleic acid components, Askew et al., J Am Chem Soc 1989, 111: 1082-90.

Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. See, e.g., DesJarlais et al., J Med Chem 1988, 31: 722-9; Meng et al., J Computer Chem 1992, 13: 505-24; Meng et al., Proteins 1993, 17: 266-78; Shoichet et al., Science 1993, 259: 1445-50.

Once a putative inhibitor of the DKK1 activity has been identified, combinatorial chemistry techniques can be employed to construct any number of variants based on the chemical structure of the identified putative inhibitor, as detailed below. The resulting library of putative inhibitors, or "test agents" may be screened using the methods of the present invention to identify test agents of the library that disrupt the DKK1 activity.

(ii) Combinatorial Chemical Synthesis:

Combinatorial libraries of test agents may be produced as part of a rational drug design program involving knowledge of core structures existing in known inhibitors of the DKK1 activity. This approach allows the library to be maintained at a reasonable size, facilitating high throughput screening. Alternatively, simple, particularly short, polymeric molecular libraries may be constructed by simply synthesizing all permutations of the molecular family making up the library. An example of this latter approach would be a library of all peptides six amino acids in length. Such a peptide library could include every 6 amino acid sequence permutation. This type of library is termed a linear combinatorial chemical library.

Preparation of Combinatorial Chemical Libraries is Well Known to Those of Skill in the Art, and may be generated by either chemical or biological synthesis. Combinatorial chemical libraries include, but are not limited to, peptide libraries (see, e.g., U.S. Pat. No. 5,010,175; Furka, Int J Pept Prot Res 1991, 37: 487-93; Houghten et al., Nature 1991, 354: 84-6). Other chemistries for generating chemical diversity libraries can also be used. Such chemistries include, but are not limited to: peptides (e.g., PCT Publication No. WO 91/19735), encoded peptides (e.g., WO 93/20242), random bio-oligomers (e.g., WO 92/00091), benzodiazepines (e.g., U.S. Pat. No. 5,288,514), diversomers such as hydantoins, benzodiazepines and dipeptides (DeWitt et al., Proc Natl Acad Sci USA 1993, 90:6909-13), vinylogous polypeptides (Hagihara et al., J Amer Chem Soc 1992, 114: 6568), non-peptidal peptidomimetics with glucose scaffolding (Hirschmann et al., J Amer Chem Soc 1992, 114: 9217-8), analogous organic syntheses of small compound libraries (Chen et al., J. Amer Chem Soc 1994, 116: 2661), oligocarbamates (Cho et al., Science 1993, 261: 1303), and/or peptidylphosphonates (Campbell et al., J Org Chem 1994, 59: 658), nucleic acid libraries (see Ausubel, Current Protocols in Molecular Biology 1995 supplement; Sambrook et al., Molecular Cloning: A Laboratory Manual, 1989, Cold Spring Harbor Laboratory, New York, USA), peptide nucleic acid libraries (see, e.g., U.S. Pat. No. 5,539,083), antibody libraries (see, e.g., Vaughan et al., Nature Biotechnology 1996, 14(3):309-14 and PCT/US96/10287), carbohydrate libraries (see, e.g., Liang et al., Science 1996, 274: 1520-22; U.S. Pat. No. 5,593,853), and small organic molecule libraries (see, e.g., benzodiazepines, Gordon E M. Curr Opin Biotechnol. 1995 Dec. 1; 6(6):624-31; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

(iii) Phage Display:

Another approach uses recombinant bacteriophage to produce libraries. Using the "phage method" (Scott & Smith, Science 1990, 249: 386-90; Cwirla et al., Proc Natl Acad Sci USA 1990, 87: 6378-82; Devlin et al., Science 1990, 249: 404-6), very large libraries can be constructed (e.g., 106-108 chemical entities). A second approach uses primarily chemical methods, of which the Geysen method (Geysen et al., Molecular Immunology 1986, 23: 709-15; Geysen et al., J Immunologic Method 1987, 102: 259-74); and the method of Fodor et al. (Science 1991, 251: 767-73) are examples. Furka et al. (14th International Congress of Biochemistry 1988, Volume #5, Abstract FR:013; Furka, Int J Peptide Protein Res 1991, 37: 487-93), Houghten (U.S. Pat. No. 4,631,211) and Rutter et al. (U.S. Pat. No. 5,010,175) describe methods to produce a mixture of peptides that can be tested as agonists or antagonists.

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

Screening for the DKK1 Binding Compound

In present invention, over-expression of DKK1 was detected in pancreatic cancer, gastric cancer, liver cancer, prostate cancer, breast cancer, bile duct cancer and cervical cancer sample, but not in normal organs (FIG. 1B). DKK1 over-expression in lung cancer and esophageal cancer is described previously (Yamabuki T et al. Cancer Res 2007; 67:2517-2525). Therefore, using the DKK1 gene, proteins encoded by the gene, the present invention provides a method of screening for a compound that binds to DKK1. Because of expression of DKK1 in pancreatic cancer, gastric cancer, liver cancer, prostate cancer, breast cancer, bile duct cancer, cervical cancer lung cancer and esophageal cancer, a compound binds to DKK1 is expected to suppress the proliferation or invasion of pancreatic cancer, gastric cancer, liver cancer, prostate cancer, breast cancer, bile duct cancer, cervical cancer lung cancer and esophageal cancer cells, and thus is useful for treating or preventing these cancers. Therefore, the present invention also provides a method for screening a compound that suppresses the proliferation or invasion of pancreatic cancer, gastric cancer, liver cancer, prostate cancer, breast cancer, bile duct cancer, cervical cancer lung cancer and esophageal cancer cells, and a method for screening a compound for treating or preventing pancreatic cancer, gastric cancer, liver cancer, prostate cancer, breast cancer, bile duct cancer, cervical cancer lung cancer and esophageal cancer using the DKK1 polypeptide. Specially, an embodiment of this screening method comprises the steps of:

(a) contacting a test compound with a polypeptide encoded by a polynucleotide of DKK1;

(b) detecting the binding activity between the polypeptide and the test compound; and (c) selecting the test compound that binds to the polypeptide.

The method of the present invention will be described in more detail below.

The DKK1 polypeptide to be used for screening may be a recombinant polypeptide or a protein derived from the nature or a partial peptide thereof. The polypeptide to be contacted with a test compound can be, for example, a purified polypeptide, a soluble protein, a form bound to a carrier or a fusion protein fused with other polypeptides.

In the context of the present invention, it was revealed that over-expression of DKK1 is detected in several cancers. Thus, by screening for test compounds that bind to DKK1, candidate compounds that have the potential to treat or prevent a cancer characterized by either or both of the over-expression and up-regulation of DKK1 can be identified. Potential of these candidate compound to treat or prevent the cancer may be evaluated by second and/or further screening to identify therapeutic agent for the cancer.

As a method of screening for proteins, for example, that bind to the DKK1 polypeptide using the DKK1 polypeptide, many methods well known by a person skilled in the art can be used. Such a screening can be conducted by, for example, immunoprecipitation method, specifically, in the following manner. The gene encoding the DKK1 polypeptide is expressed in host (e.g., animal) cells and so on by inserting the gene to an expression vector for foreign genes, such as pSV2neo, pcDNA I, pcDNA3.1, pCAGGS and pCD8. The promoter to be used for the expression may be any promoter that can be used commonly and include, for example, the SV40 early promoter (Rigby in Williamson (ed.), Genetic Engineering, vol. 3. Academic Press, London, 83-141 (1982)), the EF-alpha promoter (Kim et al., Gene 91: 217-23 (1990)), the CAG promoter (Niwa et al., Gene 108: 193 (1991)), the RSV LTR promoter (Cullen, Methods in Enzymology 152: 684-704 (1987)) the SRalpha promoter (Takebe et al., Mol Cell Biol 8: 466 (1988)), the CMV immediate early promoter (Seed and Aruffo, Proc Natl Acad Sci USA 84: 3365-9 (1987)), the SV40 late promoter (Gheysen and Fiers, J Mol Appl Genet 1: 385-94 (1982)), the Adenovirus late promoter (Kaufman et al., Mol Cell Biol 9: 946 (1989)), the HSV TK promoter and so on. The introduction of the gene into host cells to express a foreign gene can be performed according to any methods, for example, the electroporation method (Chu et al., Nucleic Acids Res 15: 1311-26 (1987)), the calcium phosphate method (Chen and Okayama, Mol Cell Biol 7: 2745-52 (1987)), the DEAE dextran method (Lopata et al., Nucleic Acids Res 12: 5707-17 (1984); Sussman and Milman, Mol Cell Biol 4: 1641-3 (1984)), the Lipofectin method (Derijard B., Cell 76: 1025-37 (1994); Lamb et al., Nature Genetics 5: 22-30 (1993): Rabindran et al., Science 259: 230-4 (1993)) and so on. The polypeptide encoded by DKK1 gene can be expressed as a fusion protein containing a recognition site (epitope) of a monoclonal antibody by introducing the epitope of the monoclonal antibody, whose specificity has been revealed, to the N- or C-terminus of the polypeptide. A commercially available epitopeantibody system can be used (Experimental Medicine 13: 85-90 (1995)).

Vectors which can express a fusion protein with, for example, beta-galactosidase, maltose binding protein, glutathione S-transferase, green fluorescence protein (GFP) and so on by the use of its multiple cloning sites are commercially available. Also, a fusion protein prepared by introducing only small epitopes from among several to a dozen amino acids so as not to change the property of the DKK1 polypeptide by the fusion is also reported. Epitopes, such as polyhistidine (His-tag), influenza aggregate HA, human c-myc, FLAG, Vesicular stomatitis virus glycoprotein (VSV-GP), T7 gene 10 protein (T7-tag), human simple herpes virus glycoprotein (HSV-tag), E-tag (an epitope on monoclonal phage) and such, and monoclonal antibodies recognizing them can be used as the epitopeantibody system for screening proteins binding to the DKK1 polypeptide (Experimental Medicine 13: 85-90 (1995)).

In immunoprecipitation, an immune complex is formed by adding these antibodies to cell lysate prepared using an appropriate detergent. The immune complex is composed of the DKK1 polypeptide, a polypeptide containing the binding ability with the polypeptide, and an antibody. Immunoprecipitation can be also conducted using antibodies against the DKK1 polypeptide, besides using antibodies against the above epitopes, which antibodies can be prepared as described above. An immune complex can be precipitated, for example by Protein A sepharose or Protein G sepharose when the antibody is a mouse IgG antibody. If the polypeptide encoded by DKK1 gene is prepared as a fusion protein with an epitope, such as GST, an immune complex can be formed in the same manner as in the use of the antibody against the DKK1 polypeptide, using a substance specifically binding to these epitopes, such as glutathione-Sepharose 4B.

Immunoprecipitation can be performed by following or according to, for example, the methods in the literature (Harlow and Lane, Antibodies, 511-52, Cold Spring Harbor Laboratory publications, New York (1988)).

SDS-PAGE is commonly used for analysis of immunoprecipitated proteins and the bound protein can be analyzed by the molecular weight of the protein using gels with an appropriate concentration. Since the protein bound to the DKK1 polypeptide is difficult to detect by a common staining method, such as Coomassie staining or silver staining, the detection sensitivity for the protein can be improved by culturing cells in culture medium containing radioactive isotope, 35S-methionine or 35S-cystein, labeling proteins in the cells, and detecting the proteins. The target protein can be purified directly from the SDS-polyacrylamide gel and its sequence can be determined, when the molecular weight of a protein has been revealed.

As a method of screening for proteins binding to the DKK1 polypeptide using the polypeptide, for example, West-Western blotting analysis (Skolnik et al., Cell 65: 83-90 (1991)) can be used. Specifically, a protein binding to the DKK1 polypeptide can be obtained by preparing a cDNA library from cultured cells (e.g., LNCaP, 22Rv1, PC-3 DU-145 and C4-2B) expected to express a protein binding to the DKK1 polypeptide using a phage vector (e.g., ZAP), expressing the protein on LB-agarose, fixing the protein expressed on a filter, reacting the purified and labeled DKK1 polypeptide with the above filter, and detecting the plaques expressing proteins bound to the DKK1 polypeptide according to the label. The polypeptide of the invention may be labeled by utilizing the binding between biotin and avidin, or by utilizing an antibody that specifically binds to the DKK1 polypeptide, or a peptide or polypeptide (for example, GST) that is fused to the DKK1 polypeptide. Methods using radioisotope or fluorescence and such may be also used.

Alternatively, in another embodiment of the screening method of the present invention, a two-hybrid system utilizing cells may be used ("MATCHMAKER Two-Hybrid system", "Mammalian MATCHMAKER Two-Hybrid Assay Kit", "MATCHMAKER one-Hybrid system" (Clontech); "HybriZAP Two-Hybrid Vector System" (Stratagene); the references "Dalton and Treisman, Cell 68: 597-612 (1992)", "Fields and Sternglanz, Trends Genet 10: 286-92 (1994)").

In the two-hybrid system, the polypeptide of the invention is fused to the SRF-binding region or GAL4-binding region and expressed in yeast cells. A cDNA library is prepared from cells expected to express a protein binding to the polypeptide of the invention, such that the library, when expressed, is fused to the VP 16 or GAL4 transcriptional activation region. The cDNA library is then introduced into the above yeast cells and the cDNA derived from the library is isolated from the positive clones detected (when a protein binding to the polypeptide of the invention is expressed in yeast cells, the binding of the two activates a reporter gene, making positive clones detectable). A protein encoded by the cDNA can be prepared by introducing the cDNA isolated above to *E. coli* and expressing the protein. As a reporter gene, for example, Ade2 gene, lacZ gene, CAT gene, luciferase gene and such can be used in addition to the HIS3 gene.

A compound binding to the polypeptide encoded by DKK1 gene can also be screened using affinity chromatography. For example, the polypeptide of the invention may be immobilized on a carrier of an affinity column, and a test compound, containing a protein capable of binding to the polypeptide of the invention, is applied to the column. A test compound herein may be, for example, cell extracts, cell lysates, etc. After loading the test compound, the column is washed, and compounds bound to the polypeptide of the invention can be prepared. When the test compound is a protein, the amino acid sequence of the obtained protein is analyzed, an oligo DNA is synthesized based on the sequence, and cDNA libraries are screened using the oligo DNA as a probe to obtain a DNA encoding the protein.

A biosensor using the surface plasmon resonance phenomenon may be used as a mean for detecting or quantifying the bound compound in the present invention. When such a biosensor is used, the interaction between the polypeptide of the invention and a test compound can be observed real-time as a surface plasmon resonance signal, using only a minute amount of polypeptide and without labeling (for example, BIAcore, Pharmacia). Therefore, it is possible to evaluate the binding between the polypeptide of the invention and a test compound using a biosensor such as BIAcore.

The methods of screening for molecules that bind when the immobilized DKK1 polypeptide is exposed to synthetic chemical compounds, or natural substance banks or a random phage peptide display library, and the methods of screening using high-throughput based on combinatorial chemistry techniques (Wrighton et al., Science 273: 458-64 (1996); Verdine, Nature 384: 11-13 (1996); Hogan, Nature 384: 17-9 (1996)) to isolate not only proteins but chemical compounds that bind to the DKK1 protein (including agonist and antagonist) are well known to one skilled in the art.

Screening: for the Compound Suppressing the Biological Activity of DKK1

In the present invention, the DKK1 protein has the activity of promoting cell proliferation of a cancer cells (FIGS. 4 and 5), cancer invasion (FIG. 3) and cancer migration (FIG. 2B). Using this biological activity as an index, the present invention provides a method for screening a compound that suppresses the proliferation, invasion or migration of pancreatic cancer, gastric cancer, liver cancer, prostate cancer, breast cancer, bile duct cancer, cervical cancer lung cancer and esophageal cancer cells, and a method for screening a compound for treating or preventing several cancers or inhibiting the metastasis, invasion or migration of pancreatic cancer, gastric cancer, liver cancer, prostate cancer, breast cancer, bile duct cancer, cervical cancer lung cancer and esophageal cancer. Thus, the present invention provides a method of screening for a compound for treating or preventing pancreatic cancer, gastric cancer, liver cancer, prostate cancer, breast cancer, bile duct cancer, cervical cancer lung cancer and esophageal cancer, or inhibiting metastasis, invasion or migration of cancer using the polypeptide encoded by DKK1 gene including the steps as follows:

(a) contacting a test compound with a polypeptide encoded by a polynucleotide of DKK1;
(b) detecting the biological activity of the polypeptide of step (a); and
(c) selecting the test compound that suppresses the biological activity of the polypeptide encoded by the polynucleotide of DKK1 as compared to the biological activity of said polypeptide detected in the absence of the test compound. The method of the present invention will be described in more detail below. Any polypeptides can be used for screening so long as they retain a biological activity of the DKK1 protein. Such biological activity includes cell-proliferating activity, invasion of cancer and cancer cell-migration of the DKK1 protein. For example, DKK1 protein can be used and polypeptides functionally equivalent to these proteins can also be used. Such polypeptides may be expressed endogenously or exogenously by cells.

The compound isolated by this screening is a candidate for antagonists of the polypeptide encoded by DKK1 gene. The term "antagonist" refers to molecules that inhibit the function of the polypeptide by binding thereto. Said term also refers to molecules that reduce or inhibit expression of the gene encoding DKK1. Moreover, a compound isolated by this screening is a candidate for compounds which inhibit the in vivo interaction of the DKK1 polypeptide with molecules (including DNAs and proteins).

When the biological activity to be detected in the present method is cell proliferation, invasion of cancer and cancer cell-migration, it can be detected, for example, by preparing cells which express the DKK1 polypeptide, culturing the cells in the presence of a test compound, and determining the speed of cell proliferation, measuring the cell cycle and such, as well as by measuring the colony forming activity, for example, shown in FIG. 4, matrigel invasion assay (described in Example) or wound migration assay (described in Examples below).

"Suppress the biological activity" as defined herein encompasses at least 10% suppression of the biological activity of DKK1 in comparison with in absence of the compound, more preferably at least 25%, 50% or 75% suppression and most preferably at 90% suppression. In the context of the present invention, it was revealed that DKK1 protein promotes following activities:
cell proliferation of a cancer cells
cancer invasion
cancer metastasis
cancer migration Thus, by screening for test compounds that suppresses these activities of a cancer characterized by either or both of the over-expression and up-regulation of DKK1, candidate compounds that have the potential to treat or prevent the cancer can be identified. Potential of these candidate compounds to treat or prevent the cancer may be evaluated by second and/or further screening to identify therapeutic agent for the cancer. For example, when a compound binding to DKK1 protein inhibits described above activities of the cancer, it may be concluded that such compound has the DKK1 specific therapeutic effect.

Screening for the Compound Altering the Expression of DKK1

In the present invention, the anti-DKK1 antibody causes inhibiting cancer cell proliferation and invasion (FIGS. 3 and 4). Therefore, a compound that inhibits the expression of DKK1 is expected to suppress the proliferation and invasion of pancreatic cancer, gastric cancer, liver cancer, prostate cancer, breast cancer, bile duct cancer, cervical cancer lung cancer and esophageal cancer cells, and thus is useful for treating or preventing these cancers, or inhibiting metastasis or invasion. Therefore, the present invention also provides a method for screening a compound that suppresses the proliferation or invasion of pancreatic cancer, gastric cancer, liver cancer, prostate cancer, breast cancer, bile duct cancer, cervical cancer lung cancer and esophageal cancer cells, and a method for screening a compound for treating or preventing pancreatic cancer, gastric cancer, liver cancer, prostate cancer, breast cancer, bile duct cancer, cervical cancer lung cancer and esophageal cancer, or inhibiting metastasis or invasion. In the context of the present invention, such screening may include, for example, the following steps:

(a) contacting a candidate compound with a cell expressing DKK1; and
(b) selecting the candidate compound that reduces the expression level of DKK1 as compared to a control.

The method of the present invention will be described in more detail below.

Cells expressing the DKK1 include, for example, cell lines established from pancreatic cancer, gastric cancer, liver cancer, prostate cancer, breast cancer, bile duct cancer, cervical cancer lung cancer and esophageal cancer; such cells can be used for the above screening of the present invention (e.g., A549, Capan-2, HPAF-11, Panc02.03, SUIT-2, HepG2, HUH-6, HUH-7, SNU-398, SNU-423, SNU-449, SNU-475, BT-549, HCC1937, MCF-7, MDA-MB-157, DU145, LNCap and PC-3). The expression level can be estimated by methods well known to one skilled in the art, for example, RT-PCR, Northern bolt assay, Western bolt assay, immunostaining and flow cytometry analysis. "Reduce the expression level" as defined herein are preferably at least 10% reduction of expression level of DKK1 in comparison to the expression level in absence of the compound, more preferably at least 25%, 50% or 75% reduced level and most preferably at 95% reduced level. The compound herein includes chemical compound, double-strand nucleotide. In the method of screening, a compound that reduces the expression level of DKK1 can be selected as candidate compounds to be used for the treatment or prevention of pancreatic cancer, gastric cancer, liver cancer, prostate cancer, breast cancer, bile duct cancer, cervical cancer lung cancer and esophageal cancer.

Alternatively, the screening method of the present invention may include the following steps:
(a) contacting a candidate compound with a cell into which a vector, composed of the transcriptional regulatory region of DKK1 and a reporter gene that is expressed under the control of the transcriptional regulatory region, has been introduced;
(b) measuring the expression or activity of said reporter gene; and
(c) selecting the candidate compound that reduces the expression or activity of said reporter gene.

Suitable reporter genes and host cells are well known in the art. Examples of suitable reporter genes include, but are not limited to, luciferase, green fluorescence protein (GFP), *Dis-* cosoma sp. Red Fluorescent Protein (DsRed), Chrolamphenicol Acetyltransferase (CAT), lacZ and beta-glucuronidase (GUS), and host cell is COS7, HEK293, HeLa and so on. The reporter construct required for the screening can be prepared by connecting reporter gene sequence to the transcriptional regulatory region of DKK1. The transcriptional regulatory region of DKK1 herein is the region from start codon to at least 500 bp upstream, preferably 1000 bp, more preferably 5000 or 10000 bp upstream. A nucleotide segment containing the transcriptional regulatory region can be isolated from a genome library or can be propagated by PCR. Methods for identifying a transcriptional regulatory region, and also assay protocol are well known (Molecular Cloning third edition chapter 17, 2001, Cold Springs Harbor Laboratory Press). The vector containing the said reporter construct is infected to host cells and the expression or activity of the reporter gene is detected by method well known in the art (e.g., using luminometer, absorption spectrometer, flow cytometer and so on). "Reduces the expression or activity" as defined herein are preferably at least 10% n reduction of the expression or activity of the reporter gene in comparison with in absence of the compound, more preferably at least 25%, 50% or 75% reduction and most preferably at 95% reduction.

In the context of the present invention, it was revealed that over-expression of DKK1 was detected in a cancer characterized by either or both of the over-expression and up-regulation of DKK1. Thus, by screening for test compounds that reduces the expression level of DKK1, candidate compounds that have the potential to treat or prevent the cancer can be identified. Potential of these candidate compounds to treat or prevent the cancer may be evaluated by second and/or further screening to identify therapeutic agent for the cancer.

EXAMPLES

Hereinafter, the present invention is described in detail with reference to Examples. However, materials, methods and such described therein only illustrate aspects of the invention and in no way are intended to limit the scope of the present invention. As such, materials, methods and such similar or equivalent to those described therein may be used in the practice or testing of the present invention.

Example I

General Methods

Cell Lines and Tissue Samples.

The 3 human lung cancer cell lines used in this study included two adenocarcinomas (A549 and PC-14), and a small-cell lung cancer (SBC-3). The human cancer cell lines used in this study were as follows; 13 pancreatic cancer cell lines (Capan-1, Capan-2, HPAF-11, KLM-1, KP-1N, Miapaca-2, Panc02.03, Panc08.13, PK-1, PK-59, PK-9, PL-45, and SUIT-2), four gastric cancer cell lines (MKN1, MKN45, MKN7, and MKN74), seven liver cancer cell lines (HepG2, HUH-6, HUH-7, SNU-398, SNU-423, SNU-449, and SNU-475), 14 breast cancer cell lines (BT-20, BT-474, BT-549, HCC1143, HCC1500, HCC1937, MCF-7, MDA-MB-157, MDA-MB-231, MDAMB-453, MDA-MB-4365, SK-BR-3, T47D, and ZR-75-1), and four prostate cancer cell lines (DU145, LNCap, PC-3, and 22RV1). All cells were grown in monolayer in appropriate media supplemented with 10% fetal calf serum (FCS) and were maintained at 37° C. in humidified air with 5% $CO_2$. Primary cancer samples had been obtained earlier with informed consent from patients undergoing curative surgery at Kanagawa Cancer Center (Kanagawa, Japan). Clinical stage was judged according to the UICC TNM classification (Diarra D et al. Nat Med. 2007; 13:156-63). This study and the use of all clinical materials mentioned were approved by individual institutional Ethical Committees.

Serum Samples.

Serum samples were obtained with written informed consent from 207 healthy control individuals. Serum samples were also obtained with informed consent from 97 colorectal cancer patients, 41 pancreatic cancer patients, 101 gastric cancer patients, 168 HCC patients, 27 prostate cancer patients, 169 breast cancer patients, 107 bile duct cancer patients, and 182 cervical cancer patients who were registered in the Japanese Project for Personalized Medicine (BioBank Japan). These serum samples from a total of 892 cancer patients were selected for the study on the basis of the following criteria: (a) patients were newly diagnosed and previously untreated and (b) their tumors were pathologically diagnosed as cancers (stages I-IV). Serum was obtained at the time of diagnosis and stored at −150 degrees C.

Semiquantitative RT-PCR.

A total of 3 micro-g aliquot of mRNA from each sample was reversely transcribed to single-stranded cDNAs using random primer (Roche Diagnostics) and Superscript II (Invitrogen, Carlsbad, Calif.). Semi-quantitative RT-PCR experiments were carried out with the following sets of synthesized primers specific to DKK1 or with beta-actin (ACTB)-specific primers as an internal control:

```
Dickkopf homolog 1 (DKK1),
5'-TAGAGTCTAGAACGCAAGGATCTC-3'      (SEQ ID NO: 3)
and

5'-CAAAAACTATCACAGCCTAAAGGG-3',    (SEQ ID NO: 4)

ACTB,
5'-GAGGTGATAGCATTGCTTTCG-3'         (SEQ ID NO: 5)
and

5'-CAAGTCAGTGTACAGGTAAGC-3'.        (SEQ ID NO: 6)
```

PCR reactions were optimized for the number of cycles to ensure product intensity to be within the linear phase of amplification.

ELISA

Serum levels of DKK1 were measured by ELISA system which had been originally constructed (20). First of all, a rabbit polyclonal antibody specific to DKK1 (Santa Cruz, Santa Cruz, Calif.) was added to a 96-well microplate (Nunc, Roskilde, Denmark) as a capture antibody and incubated for 2 hours at room temperature. After washing away any unbound antibody, 5% BSA was added to the wells and incubated for 16 hours at 4 degrees C. for blocking. After a wash, 3-fold diluted sera were added to the wells and incubated for 2 hours at room temperature. After washing away any unbound substances, a biotinylated polyclonal antibody specific for DKK1 using Biotin Labeling Kit-$NH_2$ (DOJINDO, Kumamoto, Japan) was added to the wells as a detection antibody and incubated for 2 hours at room temperature. After a wash to remove any unbound antibody-enzyme reagent, HRP-streptavidin was added to the wells and incubated for 20 minutes. After a wash, a substrate solution (R&D Systems, Inc., Minneapolis, Minn.) was added to the wells and allowed to react for 30 minutes. The reaction was stopped by adding 100 micro-1 of 2 N sulfuric acid. Color intensity was determined by a photometer at a wavelength of 450 nm, with a reference wavelength of 570 nm.

Matrigel Invasion Assay

NIH3T3 and COS-7 cells transfected either with p3XFLAG-tagged (C-terminal) plasmids expressing DKK1 or with mock plasmids were grown to near confluence in DMEM containing 10% FCS. The cells were harvested by trypsinization, washed in DMEM without addition of serum or proteinase inhibitor, and suspended in DMEM at concentration of $1 \times 10^5$ cells/ml. Before preparing the cell suspension, the dried layer of Matrigel matrix (Becton Dickinson Labware) was rehydrated with DMEM for 2 hours at room temperature. DMEM (0.75 ml) containing 10% FCS was added to each lower chamber in 24-well Matrigel invasion chambers, and 0.5 ml ($5 \times 10^4$ cells) of cell suspension was added to each insert of the upper chamber. The plates of inserts were incubated for 24 hours at 37 degrees C. After incubation the chambers were processed; cells invading through the Matrigel were fixed and stained by Giemsa as directed by the supplier (Becton Dickinson Labware, Franklin Lakes, N.J.).

Wound Migration Assay.

NIH-3T3 cells transfected either with p3XFLAG-tagged (C-terminal) plasmids expressing DKK1 or with mock plasmids were grown to near confluence in DMEM containing 1% FCS. Using a sterile 200 micro-1 pipet tip, three separate wounds were scratched on the dish, and dishes were incubated for 12 hours in DMEM containing 10% FCS at 37 degrees C. The wounds were observed at 0, 8, 12 hours.

Mice Model.

The animal experiments were conducted according to the institutional and national guidelines for the care and use of laboratory animals, and approved by the institutional animal use committee. $1 \times 10^5$ of A549 or PC-14 cells were subcutaneously implanted into the right shoulder of 6-week-old male BALB/c nude mice (nu/nu). The mice with tumor (50 mm$^2$ volume on average) were randomized into two groups and intraperitoneally administered with 100 micro-g/500 micro-1 of a rabbit polyclonal anti-human DKK1 antibody (Santa Cruz) or 100-micro-g/500 micro-1 of normal rabbit IgG (control; Santa Cruz) at days 1, 3, 5, 7, and 9 (a total of 5 injections). Tumor volume was measured once a day by using a caliper and applying the data to the formula (volume=0.52×[width]$^2$×[length]) to calculate the volume of a spheroid.

Example 2

DKK1 Expression in Various Cancers Tissues and Serum Levels in Cancer Patients

To examine the potential of DKK1 as a diagnostic biomarker for human cancer screening, the elevated expression of DKK1 transcript was first confirmed in cancer cell lines in several organs (pancreas, colon, stomach, liver, prostate, mammary glands, bile duct, and uterus). Its expression was detected by means of semiquantitative RT-PCR experiments in 5 of 13 pancreatic cancer cell lines, in 2 of 4 gastric cancer cell lines, in 7 of 7 liver cancer cell lines, in 6 of 14 breast cancer cell lines, and in 4 of 4 prostate cancer cell lines; but its transcript was barely detectable in corresponding normal tissues (FIG. 1A).

Since DKK1 protein is secreted into sera of patients with lung or esophageal cancer (Yamabuki T et al. Cancer Res 2007; 67:2517-2525), ELISA experiments were performed in serological samples from patients with various kinds of cancers. The mean (+/−1 SD) of serum DKK1 was 14.8+/−18.6 U/ml in 41 pancreatic cancer patients, 17.2+/−18.0 U/ml in 101 gastric cancer patients, 18.3+/−16.9 U/ml in 168 HCC patients, 29.7+/−25.3 U/ml in 27 prostate cancer patients, 27.0+/−22.4 U/ml in 169 breast cancer patients, 12.5+/−12.2 U/ml in 107 bile duct cancer patients, and 28.7+/−28.0 U/ml in 182 cervical cancer patients (FIG. 1B). In contrast, the mean (+/−1SD) serum levels of DKK1 in 207 healthy individuals were 6.1+/−5.0 U/ml. The levels of serum DKK1 protein were significantly higher in cancer patients than in healthy donors (P<0.001; Mann-Whitney U test), except pancreatic (P=0.286; Mann-Whitney U test) cancers. The proportions of the serum DKK1-positive cases was 34.1% for pancreatic cancer (14 of 41), 38.6% for gastric cancer (39 of 101), 53.0% for HCC (89 of 168), 55.6% for prostate cancer (15 of 27), 65.1% for breast cancer (110 of 169), 29.9% for bile duct cancer (32 of 107), and 59.3% for cervical cancer (108 of 182). The results indicated the great potential of serum DKK1 as a biomarker for detection of the great majority of cancers with various tissue origins.

Example 3

Activation of Cellular Migration by DKK1

The present inventors previously demonstrated that lung and esophageal cancer patients with DKK1-positive tumors showed shorter cancer-specific survival period than those with DKK1-negative tumors, and DKK1 has cellular invasive activity in vitro (Yamabuki T et al. Cancer Res 2007; 67:2517-2525). In this invention, the metastatic potential of cells overexpressing DKK1 was further validated. It was firstly observed by RT-PCR analysis that the DKK1 expression levels in metastatic brain tumors derived from primary lung adenocarcinoma were likely to be higher than those in primary lung adenocarcinomas (FIG. 2A). In addition, the possible role of DKK1 in cellular migration was examined by wound migration assays, using NIH3T3 cells. Transfection of DKK1 cDNA into either cell line significantly enhanced its migration activity, compared to cells transfected with mock vector (FIG. 2B).

Example 4

Inhibition of Cellular Invasive Activity by Anti-DKK1 Antibody

Because DKK1 could contribute to the highly invasive phenotype of mammalian cells (Yamabuki T et al. Cancer Res 2007; 67:2517-2525), it was investigated whether anti-DKK1 antibody (50 or 100 nM) could inhibit the invasion of COS-7 cells transfected with DKK1-expressing plasmids. Expectedly, cellular invasion caused by DKK1 over-expression was suppressed by the anti-DKK1 antibody, and the number of COS-7 cells that invaded through matrigel became almost equivalent to that of DKK1-non-transfected COS-7 cells (FIG. 3A).

The effect of anti-DKK1 antibody (50 or 100 nM) was then investigated on the lung-cancer invasive activity through Matrigel using A549 cells, which showed high levels of endogenous DKK1 expression. The cellular invasion of A549 cells detected using Matrigel assays was suppressed by addition of anti-DKK1 antibody into their culture media, in a dose-dependent manner (P<0.0001 for 100 nM, P=0.0003 for 50 nM; each paired t test; FIG. 3B), while that of PC-14 cells expressing DKK1 at a hardly-detectable level was not affected (FIG. 3C).

Example 5

Inhibition of Lung Cancer Cell Growth by Anti-DKK1 Antibody

The effect of anti-DKK1 antibody (50 or 100 nM) on the growth of A549 cells, which showed high levels of endogenous DKK1 expression was then investigated. The growth of A549 cells were suppressed by addition of anti-DKK1 antibody into their culture media, in a dose-dependent manner (P=0.006 for 100 nM, P=0.136 for 50 nM; each paired t test; FIG. 4A), while that of two lung-cancer cell lines, PC-14 and SBC-3, which scarcely expressed DKK1 was not affected (FIG. 4B).

Example 6

Inhibition of Lung Cancer Cell Growth by Anti-DKK1 Antibody in Mice

Based on the in vitro studies, the effect of anti-DKK1 antibody was examined on tumor growth in tumor transplanted mice model. Treatment of mice by intraperitoneal systemic administration with anti-DKK1 antibody (100 micro-g/500 micro-]/animal at days 1, 3, 5, 7, and 9 [a total of 5 injections]) resulted in a significant inhibition of tumor growth when compared with mice treated with the same dose of control IgG (FIG. 5A). On the other hand, the cell growth of DKK1-negative cells (PC-14) transplanted in mice was not influenced by the same dose of anti-DKK1 antibody therapy (FIG. 5B). HE staining using frozen section of the resected tumors detected significant fibrosis and decrease in viable cancer cell numbers in anti-DKK1 antibody treated tumor tissues compared with those treated with control IgG (FIG. 5C). These results revealed that the anti-DKK1 antibody had the growth suppressive effect on cancer cells in vitro and in vivo.

INDUSTRIAL APPLICABILITY

The utility of DKK1 as a diagnostic indicator of a variety of cancers is demonstrated herein. As such, the present invention provides a generalized non-invasive method for diagnosing cancer in a subject in need thereof.

The present invention further describes the use of DKK1 as a prognostic indicator of cancer. As such, the present invention provides method for assessing or determining a cancer prognosis in a subject in need thereof. Accordingly, the present invention enables clinicians to choose, in advance, the most appropriate treatment for each individual patient, even without the information of conventional clinical staging of the disease and using only routine procedures for tissue-sampling.

The present invention further describes anti-DKK1 antibodies and methods of using same to inhibit invasion, proliferation, and/or metastasis of cancer cells. Accordingly, the present invention provides methods for treating or preventing cancer using such antibodies, as well as derivatives and pharmaceutical formulations thereof.

The present invention further describes a method of screening for an anti-DKK1 antibody having potential cancer therapeutic activity comprising the step of screening a population of anti-DKK1 antibodies.

The present invention further describes a method of screening for a compound for treating or preventing a cancer.

All publications, databases, sequences, patents, and patent applications cited herein are hereby incorporated by reference.

While the invention has been described in detail and with reference to specific embodiments thereof, it will be apparent to one skilled in the art that various changes and modifications can be made therein without departing from the spirit and scope of the invention, the metes and bounds of which are set by the appended claims.

The invention claimed is:

1. A method for identifying a subject in need of therapy for a cancer, the method comprising:
   (a) contacting an antibody against DKK1 protein with a blood or blood derived sample from a subject suspected of suffering from a cancer selected from the group consisting of pancreatic cancer, gastric cancer, prostate cancer, bile duct cancer and cervical cancer to determine a blood concentration of a DKK1 protein in the blood or blood derived sample;
   (b) obtaining a biological sample comprising pancreatic, gastric, prostate, bile duct, or cervical tissue from the subject by surgery or biopsy if the blood concentration of DKK1 protein in the blood or blood derived sample from the subject is greater than a normal control level in a blood or a blood derived sample; and
   (c) determining the level of DKK1 protein in the biological sample, and
   (d) identifying the subject in need of therapy for a cancer if the level of DKK1 protein in the biological sample is greater than the level in a control biological sample comprising pancreatic, gastric, prostate, bile duct, or cervical tissue.

2. The method of claim 1, wherein the blood concentration of DKK1 protein in the blood or blood derived sample is at least 10% greater than the normal control level.

3. The method of claim 1, wherein the blood concentration of DKK1 protein in the blood or blood derived sample is determined by an immunoassay.

4. The method of claim 3, wherein the immunoassay is an ELISA.

5. A method of diagnosing a cancer in pancreatic, gastric, prostate, bile duct, or cervical tissue in a subject, the method comprising:
   (a) obtaining a biological sample from a subject selected from the group consisting of pancreatic, gastric, prostate, bile duct, and cervical tissue;
   (b) contacting an antibody against DKK1 protein with the biological sample collected in step (a) to determine a level of DKK1 protein in the biological sample;
   (c) providing a diagnosis that the subject suffers from pancreatic cancer, gastric cancer, prostate cancer, bile duct cancer, or cervical cancer if the level of DKK1 protein in the biological sample from the subject is greater than a normal control level.

6. The method of claim 1 or 5, wherein the level of DKK1 protein in the biological sample from the subject is at least 10% greater than the normal control level.

* * * * *

UNITED STATES PATENT AND TRADEMARK OFFICE
CERTIFICATE OF CORRECTION

PATENT NO. : 8,709,731 B2
APPLICATION NO. : 12/674660
DATED : April 29, 2014
INVENTOR(S) : Nakamura et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 565 days.

Signed and Sealed this
Twenty-ninth Day of September, 2015

Michelle K. Lee
*Director of the United States Patent and Trademark Office*

SEQUENCE LISTING

```
<160> NUMBER OF SEQ ID NOS: 6

<210> SEQ ID NO 1
<211> LENGTH: 1518
<212> TYPE: DNA
<213> ORGANISM: Homo sapiens
<220> FEATURE:
<221> NAME/KEY: CDS
<222> LOCATION: (138)..(938)

<400> SEQUENCE: 1
ctgcagtcag gactctggga ccgcaggggg ctcccggacc ctgactctgc agccgaaccg      60
gcacggtttc gtggggaccc aggcttgcaa agtgacggtc attttctctt tctttctccc     120
tcttgagtcc ttctgag atg atg gct ctg ggc gca gcg gga gct acc cgg       170
                   Met Met Ala Leu Gly Ala Ala Gly Ala Thr Arg
                    1               5                  10 gtc ttt gtc gcg atg gta gcg gcg gct ctc ggc ggc cac cct ctg ctg      218
Val Phe Val Ala Met Val Ala Ala Ala Leu Gly Gly His Pro Leu Leu
             15                  20                  25 gga gtg agc gcc acc ttg aac tcg gtt ctc aat tcc aac gct atc aag      266
Gly Val Ser Ala Thr Leu Asn Ser Val Leu Asn Ser Asn Ala Ile Lys
         30                  35                  40 aac ctg ccc cca ccg ctg ggc ggc gct gcg ggg cac cca ggc tct gca      314
Asn Leu Pro Pro Pro Leu Gly Gly Ala Ala Gly His Pro Gly Ser Ala
     45                  50                  55 gtc agc gcc gcg ccg gga atc ctg tac ccg ggc ggg aat aag tac cag      362
Val Ser Ala Ala Pro Gly Ile Leu Tyr Pro Gly Gly Asn Lys Tyr Gln
```

```
                60                  65                  70                  75
acc att gac aac tac cag ccg tac ccg tgc gca gag gac gag gag tgc       410
Thr Ile Asp Asn Tyr Gln Pro Tyr Pro Cys Ala Glu Asp Glu Glu Cys
                80                  85                  90 ggc act gat gag tac tgc gct agt ccc acc cgc gga ggg gac gca ggc       458
Gly Thr Asp Glu Tyr Cys Ala Ser Pro Thr Arg Gly Gly Asp Ala Gly
                95                 100                 105 gtg caa atc tgt ctc gcc tgc agg aag cgc cga aaa cgc tgc atg cgt       506
Val Gln Ile Cys Leu Ala Cys Arg Lys Arg Arg Lys Arg Cys Met Arg
               110                 115                 120 cac gct atg tgc tgc ccc ggg aat tac tgc aaa aat gga ata tgt gtg       554
His Ala Met Cys Cys Pro Gly Asn Tyr Cys Lys Asn Gly Ile Cys Val
           125                 130                 135 tct tct gat caa aat cat ttc cga gga gaa att gag gaa acc atc act       602
Ser Ser Asp Gln Asn His Phe Arg Gly Glu Ile Glu Glu Thr Ile Thr
140                 145                 150                 155 gaa agc ttt ggt aat gat cat agc acc ttg gat ggg tat tcc aga aga       650
Glu Ser Phe Gly Asn Asp His Ser Thr Leu Asp Gly Tyr Ser Arg Arg
                160                 165                 170 acc acc ttg tct tca aaa atg tat cac acc aaa gga caa gaa ggt tct       698
Thr Thr Leu Ser Ser Lys Met Tyr His Thr Lys Gly Gln Glu Gly Ser
                175                 180                 185 gtt tgt ctc cgg tca tca gac tgt gcc tca gga ttg tgt tgt gct aga       746
Val Cys Leu Arg Ser Ser Asp Cys Ala Ser Gly Leu Cys Cys Ala Arg
                190                 195                 200 cac ttc tgg tcc aag atc tgt aaa cct gtc ctg aaa gaa ggt caa gtg       794
His Phe Trp Ser Lys Ile Cys Lys Pro Val Leu Lys Glu Gly Gln Val
           205                 210                 215 tgt acc aag cat agg aga aaa ggc tct cat gga cta gaa ata ttc cag       842
Cys Thr Lys His Arg Arg Lys Gly Ser His Gly Leu Glu Ile Phe Gln
220                 225                 230                 235 cgt tgt tac tgt gga gaa ggt ctg tct tgc cgg ata cag aaa gat cac       890
Arg Cys Tyr Cys Gly Glu Gly Leu Ser Cys Arg Ile Gln Lys Asp His
                240                 245                 250 cat caa gcc agt aat tct tct agg ctt cac act tgt cag aga cac taa       938
His Gln Ala Ser Asn Ser Ser Arg Leu His Thr Cys Gln Arg His
           255                 260                 265 accagctatc caaatgcagt gaactccttt tatataatag atgctatgaa aacctttat     998 gaccttcatc aactcaatcc taaggatata caagttctgt ggtttcagtt aagcattcca   1058
ataccacctt ccaaaaacct ggagtgtaag agctttgttt ctttatggaa ctcccctgtg   1118
attgcagtaa attactgtat tgtaaattct cagtgtggca cttacctgta aatgcaatga   1178 aactttttaat tattttttcta aaggtgctgc actgcctatt tttcctcttg ttatgtaaat  1238
ttttgtacac attgattgtt atcttgactg acaaatattc tatattgaac tgaagtaaat   1298
catttcagct tatagttctt aaaagcataa ccctttaccc catttaattc tagagtctag   1358
aacgcaagga tctcttggaa tgacaaatga taggtaccta aaatgtaaca tgaaaatact   1418
agcttatttt ctgaaatgta ctatcttaat gcttaaatta tatttcccctt taggctgtga  1478 tagtttttga aataaaattt aacatttaaa aaaaaaaaa                          1518

<210> SEQ ID NO 2
<211> LENGTH: 266
<212> TYPE: PRT
<213> ORGANISM: Homo sapiens

<400> SEQUENCE: 2

Met Met Ala Leu Gly Ala Ala Gly Ala Thr Arg Val Phe Val Ala Met
1               5                   10                  15
```

-continued

Val Ala Ala Leu Gly Gly His Pro Leu Gly Val Ser Ala Thr
        20                  25                  30

Leu Asn Ser Val Leu Asn Ser Asn Ala Ile Lys Asn Leu Pro Pro Pro
            35                  40                  45

Leu Gly Gly Ala Ala Gly His Pro Gly Ser Ala Val Ser Ala Ala Pro
    50                  55                  60

Gly Ile Leu Tyr Pro Gly Gly Asn Lys Tyr Gln Thr Ile Asp Asn Tyr
65                  70                  75                  80

Gln Pro Tyr Pro Cys Ala Glu Asp Glu Glu Cys Gly Thr Asp Glu Tyr
                85                  90                  95

Cys Ala Ser Pro Thr Arg Gly Gly Asp Ala Gly Val Gln Ile Cys Leu
            100                 105                 110

Ala Cys Arg Lys Arg Lys Arg Cys Met Arg His Ala Met Cys Cys
        115                 120                 125

Pro Gly Asn Tyr Cys Lys Asn Gly Ile Cys Val Ser Ser Asp Gln Asn
        130                 135                 140

His Phe Arg Gly Glu Ile Glu Thr Ile Thr Glu Ser Phe Gly Asn
145                 150                 155                 160

Asp His Ser Thr Leu Asp Gly Tyr Ser Arg Arg Thr Thr Leu Ser Ser
                165                 170                 175

Lys Met Tyr His Thr Lys Gly Gln Glu Gly Ser Val Cys Leu Arg Ser
            180                 185                 190

Ser Asp Cys Ala Ser Gly Leu Cys Cys Ala Arg His Phe Trp Ser Lys
        195                 200                 205

Ile Cys Lys Pro Val Leu Lys Glu Gly Gln Val Cys Thr Lys His Arg
        210                 215                 220

Arg Lys Gly Ser His Gly Leu Glu Ile Phe Gln Arg Cys Tyr Cys Gly
225                 230                 235                 240

Glu Gly Leu Ser Cys Arg Ile Gln Lys Asp His His Gln Ala Ser Asn
                245                 250                 255

Ser Ser Arg Leu His Thr Cys Gln Arg His
            260                 265

<210> SEQ ID NO 3
<211> LENGTH: 24
<212> TYPE: DNA
<213> ORGANISM: Artificial
<220> FEATURE:
<223> OTHER INFORMATION: primer (RT-PCR)

<400> SEQUENCE: 3
tagagtctag aacgcaagga tctc                                              24

<210> SEQ ID NO 4
<211> LENGTH: 24
<212> TYPE: DNA
<213> ORGANISM: Artificial
<220> FEATURE:
<223> OTHER INFORMATION: primer (RT-PCR)

<400> SEQUENCE: 4
caaaaactat cacagcctaa aggg                                              24

<210> SEQ ID NO 5
<211> LENGTH: 21
<212> TYPE: DNA
<213> ORGANISM: Artificial
<220> FEATURE:
<223> OTHER INFORMATION: primer (RT-PCR)

```
<400> SEQUENCE: 5
gaggtgatag cattgctttc g                                              21

<210> SEQ ID NO 6
<211> LENGTH: 21
<212> TYPE: DNA
<213> ORGANISM: Artificial
<220> FEATURE:
<223> OTHER INFORMATION: primer (RT-PCR)

<400> SEQUENCE: 6
caagtcagtg tacaggtaag c                                              21
```